(12) United States Patent
Souza

(10) Patent No.: US 6,379,661 B1
(45) Date of Patent: *Apr. 30, 2002

(54) PHARMACEUTICAL COMPOSITIONS COMPRISING PLURIPOTENT GRANULOCYTE COLONY-STIMULATING FACTOR

(75) Inventor: Lawrence M. Souza, Thousand Oaks, CA (US)

(73) Assignee: Amen Inc., Thousand Oaks, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/430,103

(22) Filed: Oct. 29, 1999

Related U.S. Application Data

(63) Continuation of application No. 09/060,275, filed on Apr. 14, 1998, now Pat. No. 6,004,548, which is a division of application No. 08/679,897, filed on Jul. 15, 1996, now Pat. No. 5,830,705, which is a continuation of application No. 08/452,135, filed on May 26, 1995, now Pat. No. 5,582,823, which is a division of application No. 08/243,556, filed on May 16, 1994, now abandoned, which is a continuation of application No. 08/065,465, filed on May 20, 1993, now abandoned, which is a continuation of application No. 07/269,885, filed on Nov. 10, 1988, now abandoned, which is a division of application No. 06/835,548, filed on Mar. 3, 1986, now Pat. No. 4,810,643, which is a continuation-in-part of application No. 06/768,959, filed on Aug. 23, 1985, now abandoned.

(51) Int. Cl.$^7$ ............................................... A61K 38/18
(52) U.S. Cl. ............................. 424/85.1; 514/2; 514/12
(58) Field of Search ....................... 514/2, 12; 424/85.1

(56) References Cited

U.S. PATENT DOCUMENTS

| | | | |
|---|---|---|---|
| 4,358,535 A | 11/1982 | Falkow et al. | 435/5 |
| 4,394,443 A | 7/1983 | Weissman et al. | 435/6 |
| 4,810,643 A | * 3/1989 | Souza | |
| 4,833,127 A | 5/1989 | Ono et al. | 514/21 |
| 4,904,584 A | 2/1990 | Shaw | 530/531 |
| 4,999,291 A | 3/1991 | Souza | 435/69.1 |
| 5,580,775 A | * 12/1996 | Souza | |
| 5,582,823 A | 12/1996 | Souza | 424/85.2 |
| 5,830,705 A | 11/1998 | Souza | 435/69.5 |
| 6,004,548 A | 12/1999 | Souza | 424/85.1 |

FOREIGN PATENT DOCUMENTS

| | | |
|---|---|---|
| EP | 0 109 748 | 5/1984 |
| EP | 136490 | 4/1985 |
| EP | A1 0 169 566 | 1/1986 |
| EP | 0 215 126 A | 3/1987 |
| EP | 0 220 520 A | 5/1987 |
| GB | 2 130 219 | 1/1986 |
| JP | 23777-85 | 2/1985 |
| JP | 206066-85 | 9/1985 |
| JP | 209638/85 | 9/1985 |
| JP | 217150/85 | 9/1985 |
| WO | WO 83/04053 | 11/1983 |
| WO | WO 85/00817 | 2/1985 |
| WO | WO 85/02610 | 6/1985 |
| WO | WO 86/04506 | 8/1986 |
| WO | WO 86/04605 | 8/1986 |

OTHER PUBLICATIONS

Baron et al., "Antibodies against the chemically synthesized genome–linked protein of poliovirus react with native virus–specific proteins," Cell, 28, pp. 395–404 (1982).

Benton et al., "Screening λgt recombinant clones by hybridization to single plaques in situ," Science, 196, pp. 180–182 (1977).

Broxmeyer et al., "Cell–free granulocyte colony inhibiting activity derived from human polymorphonuclear neutrophils," Exp. Hemat., 5, pp. 87–102, (1977).

Burgess et al., "Purification and properties of colony–stimulating factor from mouse lung–conditioned medium," The Journal of Biological Chemistry, 252, No. 6, pp. 1998–2003 (1977).

Burgess et al., "Characterization of a serum factor stimulating the differentiation of myelomonocytic leukemic cells," In. J. Cancer, 26, pp. 647–654 (1980).

Caruthers et al., "New methods for synthesizing deoxyoligonucleotides," Department of Chemistry, University of Colorado, Boulder, CO 80309, pp. 1–17 (1982).

Chirgwin et al., "Isolation of biologically active ribonucleic acid from sources enriched in ribonuclease," Biochemistry, 18, No. 24, pp. 5294–5299 (1979).

Das et al., "Human colony–stimulating factor (CSF–1) radioimmunoassay: resolution of three subclasses of human colony–stimulating factors," Blood, 58, No. 3, pp. 630–641 (1981).

Davis et al., A Manual for Genetic Engineering, Advanced Bacterial Genetics, Cold Spring Harbor Laboratory, Cold Spring Harbor, NY, pp. 55–58 & 174–176 (1980).

(List continued on next page.)

Primary Examiner—Elizabeth C. Kemmerer
(74) Attorney, Agent, or Firm—Marshall, Gerstien & Borun

(57) ABSTRACT

Disclosed are novel polypeptides possessing part or all of the primary structural conformation and one or more of the biological properties of a mammalian (e.g., human) pluripotent granulocyte colony-stimulating factor ("hpG-CSF") which are characterized in preferred forms by being the product of procaryotic or eucaryotic host expression of an exogenous DNA sequence. Sequences coding for part or all of the sequence of amino acid residues of hpG-CSF or for analogs thereof may be incorporated into autonomously replicating plasmid or viral vectors employed to transform or transfect suitable procaryotic or eucaryotic host cells such as bacteria, yeast or vertebrate cells in culture. Products of expression of the DNA sequences display, e.g., the physical and immunological properties and in vitro biological activities of isolates of hpG-CSF derived from natural sources. Disclosed also are chemically synthesized polypeptides sharing the biochemical and immunological properties of hpG-CSF.

3 Claims, 16 Drawing Sheets

OTHER PUBLICATIONS

Dexter et al., "The role of growth factors in haemopoiesis," *BioEssays,* 2, No. 4, pp. 154–158 (1985).

Dreesman et al., "Antibody to hepatitis B surface antigen after a single inoculation of uncoupled synthetic HBsAg peptides," *Nature,* 295, pp. 158–160 (1982).

Gough et al., "Molecular cloning of cDNA encoding a murine haematopoietic growth regulator, granulocyte—marcophage colony stimulation factor," *Nature,* 309, pp. 763–767 (1984).

Green et al., "Immunogenic structure of the influenza virus hemaglutinin," *Cell,* 28, pp. 477–487 (1982).

Hanahan, "Studies on transformation of *Escherichia coli* with plasmids," *J. Mol. Biol.,* 166, pp. 557–580 (1983).

Hewick et al., "A gas–liquid solid phase peptide and protein sequenator," *The Journal of Biological Chemistry,* pp. 7990–7997 (1981).

Ihle et al., "Procedures for the purification of interleukin 3 to homogeneity," *The Journal of Immunology,* 129, No. 6, pp. 2431–2436 (1982).

Jaye et al., "Isolation of a human anti–haemophilic factor IX cDNA clone using a unique 52–base synthetic oligonucleotide probe deducted from the amino acid sequence of bovine factor IX," *Nucleic Acids Research,* 11, No. 8, pp. 2325–2335 (1983).

Kaiser et al., "Amphiphilic secondary structure: design of peptide hormones," *Science,* 223, pp. 249–255 (1984).

Lai, "Technical improvements in protein microsequencing," *Analytica Chimica Acta,* 163, pp. 243–248 (1984).

Lawn et al., "The isolation and characterization of linked δ– and β–globin genes from a cloned library of human DNA," *Cell,* 15, pp. 1157–1174 (1978).

Lee et al., "Isolation of cDNA for a human granulocyte–macrophage colony–stimulating factor by functional expression in mammalian cells," *Proc. Natl. Acad. Sci. USA,* 82, pp. 4360–4364 (1985).

Lerner et al., "Antibodies to chemically synthesized peptides predicted from DNA sequences as probes of gene expression," *Cell,* 23, pp. 309–310 (1981).

Lerner et al., "Chemically synthesized peptides predicted from the nucleotide sequence of the hepatitis B virus genome elicit antibodies reactive with the native envelope protein of Dane particles," *Proc. Natl. Acad. Sci. USA,* 78, pp. 3403–3407 (1981).

Lerner, "A short chain of amino acids assembled in the laboratory to mimic a site on the surface of a viral protein can give rise to antibodies of predetermined specificity that confer immunity against the virus," *Synthetic Vaccines,* pp. 66–74 (undated).

Lu et al., "Association of cell cycle expression of Ia–like antigenic determinants on normal human multipotential (CFU–GEMM) and erythroid (BFU–E) progenitor cells with regulation in vitro by acidic isoferritins," *Blood,* 61, No. 2, pp. 250–156 (1983).

Maniatis et al., "Amplification and characterization of a β–globin gene synthesized in vitro," *Cell,* 8, pp. 163–182 (1976).

Metcalf, "Clonal extinction of myelomonocytic leukemic cells by serum from mice injected with endotoxin," *Int. J. Cancer,* 25, pp. 225–233 (1980).

Metcalf et al., "Autoinduction of differentiation in WEHI–3B leukemia cells," *Int. J. Cancer,* 30, pp. 773–780 (1982).

Metcalf, "The granulocyte–macrophage colony–stimulating factors," *Science,* 229, pp. 16–22 (1985).

Nicola et al., "Purification of a factor inducing differentiation in murine myelomonocytic leukemia cells," *The Journal of Biological Chemistry,* 258, No. 14, pp. 9017–9023 (1983).

Nicola et al., "Binding of the differentiation–inducer, granulocyte–colony–stimulating factor, to responsive but not unresponsive leukemic cell lines," *Proc. Natl. Acad. Sci. USA,* 81, pp. 3765–3769 (1984).

Nicola et al., "Hemopoietic colony–stimulating factors," *Immunology Today,* 5, No. 3, pp. 76–80 (1984).

Nicola et al., "Identification of the human analogue of a regulator that induces differentiation in murine leukaemic cells," *Nature,* 314, pp. 625–628 (1985).

Nigg et al., "Immunofluorescent localization of the transforming protein of Rous sarcoma virus with antibodies against a synthetic src peptide," *Proc. Natl. Acad. Sci. USA,* 79, pp. 5322–5326 (1982).

Okayama et al., "A cDNA cloning vector that permits expression of cDNA inserts in mammalian cells," *Molecular and Cellular Biology,* pp. 280–289 (1983).

Okayama et al., "High–efficiency cloning of full–length cDNA," *Molecular and Cellular Biology,* pp. 161–170 (1982).

Palmiter et al., "Metallothionein–human GH fusion genes stimulate growth of mice," *Science,* 222, pp. 809–814 (1983).

Payvar et al., "Methylmercury hydroxide enhancement of translation and transcription of ovalbumin and conalbumin mRNA's," *The Journal of Biological Chemistry,* 254, No. 16, pp. 7636–7642 (1979).

Reyes et al., "Isolation of a cDNA clone for the murine transplantation antigen H–2K$^b$," *Proc. Natl. Acad. Sci., USA,* 79, pp. 3270–3274 (1982).

Ross et al., "Phosphotyrosine–containing proteins isolated by affinity chromatography with antibodies to a synthetic hapten," *Nature,* 294, pp. 654–656 (1981).

Sachs, L. "Growth, Differentiation and the Reversal of Malignancy," *Scientific American,* 254(1):40–47 (1986).

Sanger et al., "DNA sequencing with chain–terminating inhibitors," *Proc. Natl. Acad. Sci. USA,* 74, No. 12, pp. 5463–5467 (1977).

Takahashi et al., "Molecular cloning of the human cholecystokinin gene by use of a synthetic probe containing dioxyinosine," *Proc. Natl. Acad. Sci. USA,* 82, pp. 1931–1935 (1985).

Tejedor et al., "Iodination of biological samples without loss of functional activity," *Analytical Biochemistry,* 127, pp. 143–149 (1982).

Tramontano et al., "Statistical evaluation of the coding capacity of complementary DNA strands," *Nucleic Acids Research,* 12, No. 12, pp. 5049–5059 (1984).

Venuta et al., "Production and regulation of interleukin–2 in human lymphoblastic leukemias studied with T–cell monoclonal antibodies," *Blood,* 61, No. 4, pp. 781–789 (1983).

Wahl et al., "Efficient transfer of large DNA fragments from agarose gels to diazobenzyloxymethyl–paper and rapid hybridization by using dextran sulfate," *Proc. Natl. Acad. Sci. USA,* 76, No. 8, pp. 3683–3687 (1979).

Wallace et al., "Hybridization of synthetic oligodeoxyribonucleotides to $\Phi_x$ 174 DNA: the effect of single base pair mismatch," *Nucleic Acids Research,* 6, No. 11, pp. 3543–3557 (1979).

Walter et al., "Antibodies specific for the carboxy- and amino-terminal regions of simian virus 40 large tumor antigen," *Proc. Natl. Acad. Sci. USA,* 77, No. 9, pp. 5970–5200 (1980).

Walter et al., "Antibodies specific for the polyoma virus middle-size tumor antigen," *Proc. Natl. Acad. Sci. USA,* 78, No. 8, pp. 4882–4886 (1981).

Weiland et al., "In vivo activity of asialo-erythropoietin in combination with asialo-glycoproteins," *Blut,* 44, pp. 173–175 (1982).

Welte et al., "Purification and biochemical characterization of two differentiation inducing proteins for leukemic cells produced by a bladder carcinoma cell line," Abstract No. 0287, *Leukemia 1985,* p. 116 (1985).

Welte et al., "Purification and biochemical characterization of two differentiation inducing proteins for leukemic cells produced by the bladder carcinoma cell line 5637," *Leukemia: Recent Advances in Biology and Treatment,* Proceedings of a UCLA Symposium held in Keystone, Colorado, Jan. 27–Feb. 2, 1985, Gale et al., (eds.), Alan R. Liss, Inc., New York, pp. 339–347 (1985).

Welte et al., "Purification and biochemical characterization of human pluripotent hematopoietic colony-stimulating factor," *Proc. Natl. Acad. Sci. USA,* 82, pp. 1526–1530 (1985).

Wigler et al., "Biochemical transfer of single-copy eucaryotic genes using total cellular DNA as donor," *Cell,* 14, pp. 725–731 (1978).

Wong et al., "Synthetic peptide fragment of src gene product inhibits the src protein kinase and crossreacts immunologically with avian one kinases and cellular phosphoproteins," *Proc. Natl. Acad. Sci. USA,* 78, No. 12, pp. 7412–7416 (1981).

Wong et al., "Human GM–CSF: molecular cloning of the complementary DNA and purification of the natural and recombinant proteins," *Science,* 228, pp. 810–815 (1985).

Yokota et al., "Isolation and characterization of a mouse cDNA clone that expresses mast-cell growth-factor activity in monkey cells," *Proc. Natl. Acad. Sci. USA,* 81, pp. 1070–1074 (1984).

Bird, "DNA methylation and the frequency of CpG in animal DNA," *Nucleic Acids Res.,* 8, pp. 1499–1504 (1980).

Clark-Lewis et al., "Purification to apparent homogeneity of a factor stimulating the growth of multiple lineages of hemopoietic cells," *J. Biol. Chem.,* 259, pp. 7488–7494 (1984).

DeLamarter et al., "Recombinant murine GM–CSF from *E. coli* has biological activity and is neutralized by a specific antiserum," *EMBO Journal,* 4, No. 10, pp. 2575–2581 (1985).

Glover, *DNA Cloning,* vols. 1 & 2, pp. 191–211 and 213–239 (1985).

Glover, "The mechanics of DNA manipulation," *Gene Cloning,* pp. 179–213 (1984).

Grantham et al., "Codon catalog usage is a genome strategy modulated for gene expressivity," *Nucleic Acids Res.,* 9, No. 1, pp. 43–74 (1981).

Gray et al., Expression of human immune interferon cDNA in *E. coli* and monkey cells, *Nature,* 295, pp. 503–508 (1982).

Hunkapiller et al., "Protein sequence analysis: automated microsequencing," *Science,* 219, pp. 650–654, 659 (1983).

Lathe, "Synthetic oligonucleotide probes deduced from amino acid sequence data," *J. Mol. Biol.,* 183, pp. 1–12 (1985).

Marasco et al., "Substance P binds to the formylpeptide chemotaxis receptor on the rabbit neutrophil," *Biochem. and Biophy. Res. Comm.,* 99, No. 4, pp. 1065–1072 (1981).

March et al., "Cloning, sequence and expression of two distinct human interleukin-1 complementary DNAs," *Nature,* 315, pp. 641–647 (1985).

Nagata et al., "The chromosomal gene structure and two mRNAs for human granulocyte colony-stimulating factor," *EMBO Journal,* 5, No. 3, pp. 575–581 (1986).

Nagata et al., "Molecular cloning and expression of cDNA for human granulocyte colony-stimulating factor," *Nature,* 319, pp. 415–418 (1986).

Wang et al., "Molecular cloning of the complementary DNA for human tumor necrosis factor," *Science,* 228, pp. 149–154 (1985).

Welte et al., "Purification to apparent homogeneity and biochemical characterization of human pluripotent hematopoietic colony-stimulating factor," *Haematology and Blood Transfusion,* 29, pp. 398–401 (1985).

Welte et al., "Purification and biochemical characterization of human pluripotent hematopoietic colony-stimulating factor produced by a human bladder carcinoma cell line," Abstract, *Lymphokine Res. 3,* 4, p. 281 (1984).

Zsebo et al.,m "Recombinant human granulocyte colony stimulating factor: molecular and biological characterization," *Immunobiol.,* 172, pp. 175–184 (1986).

Tsuneoka et al., "A granulocyte colony-stimulating factor from serum-free cultures of RSP-2-P3 cells: its separation from a macrophage colony-stimulating factor and its biological and molecular characterization," *Cell Struct. and Funct.,* 9, pp. 67–81 (1984).

Suggs et al., "Use of synthetic oligonucleotides as hybridization probes: isolation of cloned cDNA sequences for human $\beta_3$–microglobulin," *Proc. Nat'l Acad. Sci. USA,* 78, pp. 6613–6617 (1981).

Nomura et al., "Purification and characterization of human granulocyte colony–stimulating factor," *EMBO J.,* 5:871–876 (1986).

Kawasaki et al., Molecular cloning of a complementary DNA encoding human marcophage–specific colony–stimulating factor (CSF–1), *Science,* 230, pp. 291–296 (1985).

Miura et al., "Use of the deoxyinosine–containing probe to isolate and sequence cDNA encoding the fusion (F) glycoprotein of Sendai virus (HVJ)," *Gene,* 38, pp. 271–274 (1985).

Takahashi et al., "Molecular cloning of the human cholecystokinin (CCK) gene and its structure," 7th Annual Meeting of the Molecular Biology Society of Japan, Dec., 1974.

Taniguchi et al., "Construction and identification of a bacterial plasmid containing the human fibroblast interferon gene sequence," *Proc. Jpn. Acad.,* 55(B), pp. 464–469 (1979).

Nagata et al., "Synthesis in *E. coli* of a polypeptide with human leukocyte interferon activity," *Nature,* 284, pp. 316–320 (1980).

Taniguchi et al., "Structure and expression of a cloned cDNA for human interleukin–2," *Nature,* 302, pp. 305–310 (1983).

Lomedico et al., "Cloning and expression of murine interleukin–1 cDNA in *Escherichia coli,*" *Nature,* 312, pp. 458–462 (1984).

Gray et al., "Cloning and expression of a cDNA for human lymphotoxin, a lymphokine with tumour necrosis activity," *Nature,* 312, pp. 721–724 (1984).

Pennica et al., "Human tumour necrosis factor: precursor structure, expression and homology to lymphotoxin," *Nature*, 312, pp. 724–729 (1984).

Auron et al., "Nucleotide sequence of human monocyte interleukin 1 precursor cDNA," *Proc. Natl. Acad. Sci. USA*, 81, pp. 7907–7911 (1984).

Furutani et al., "Cloning and characterization of the cDNAs for human and rabbit interleukin–1 precursor," *Nucleic Acids Res.*, 13, No. 16, pp. 5869–5882 (1985).

Fung et al., "Molecular cloning of cDNA for murine interleukin–3," *Nature*, 307, pp. 233–237 (1984).

Cantrell et al., "Cloning, sequence, and expression of a human granulocyte/macrophage colony–stimulating factor," *Proc. Natl. Acad. Sci. USA*, 82, pp. 6250–6254 (1985).

Jacobs et al., "Isolation and characterization of genomic and cDNA clones of human erythropoietin," *Nature*, 313, pp. 806–810 (1985).

Cameron et al., "Amino acid sequence analysis of human interleukin 1 (IL–1)," *J. Exp. Med.*, 162, pp. 790–801 (1985).

Beutler et al., "Identity of tumour necrosis factor and the macrophage–secreted factor cachectin," *Nature*, 316, pp. 552–554 (1985).

Jong et al., "The CDC8 gene of yeast encodes thymidylate kinase," *The Journal of Biological Chemistry*, 259, pp. 11052–11059 (1984).

Nikaido et al., "Molecular cloning of cDNA encoding human interleukin–2 receptor," *Nature*, 311, pp. 631–635 (1984).

Baird et al., "Retina– and eye–derived endothelial cell growth factors: partial molecular characterization and identity with acidic and basic fibroblast growth factors," *Biochem.*, 24, No. 27, pp. 7855–7860 (1985).

Jacobs et al., "Isolation and characterization of genomic and cDNA clones of human erythropoietin," *Nature*, 313, pp. 806–809 (1985).

Ebina et al., "The human insulin receptor cDNA: the structural basis for hormone–activated transmembrane signalling," *Cell*, 40, pp. 747–758 (1985).

Minamino et al., "Neuromedin U–8 and U–25: novel uterus stimulating and hypertensive peptides identified in porcine spinal cord," *Biochemical and Biophysical Research Communications*, 130, No. 3, pp. 1078–1085 (1985).

Yoshinaka et al., "Translational readthrough of an amber termination codon during synthesis of feline leukemia virus protease," *Journal of Virology*, 55, pp. 870–873 (1985).

Lee et al., "Biochemical characterization of the 94– and 78–kilodalton glucose–regulated proteins in hamster fibroblasts," *The Journal of Biological Chemistry*, 259, No. 7, pp. 4616–4621 (1984).

Esch et al., "Characterization of a 40 residue peptide from a human pancreatic tumor with growth hormone releasing activity," *Biochemical and Biophysical Research Communications*, 109, No. 1, pp. 152–158 (1982).

Bohlen et al., "Human brain fibroblast growth factor," *FEBS Letters*, 185, No. 1, pp. 177–181 (1985).

Broze, Jr. et al., "Purification of human brain tissue factor," *The Journal of Biological Chemistry*, 260, No. 20, pp. 10917–10920 (1985).

Ohtsuka et al., "An alternative approach to deoxyoligonucleotides as hybridization probes by insertion of deoxyinosine at ambiguous codon positions," *J. Biol. Chem.*, 260, No. 5, pp. 2605–2608 (1985).

Ohkubo et al., "Cloning and sequence analysis of cDNA for rat antiotensinogen," *Proc. Natl. Acad. Sci. USA*, 80, pp. 2196–2200 (1983).

Liang et al., "Characterization of human interleukin 2 derived from *Escherichia coli*," *Biochem. J*, 229, pp. 429–439 (1985).

Derynck et al., "Human transforming growth factor–α: precursor structure and expression in *E. coli*," *Cell*, 38, pp. 287–297 (1984).

Ullrich et al., "Human epidermal growth factor receptor cDNA sequence and aberrant expression of the amplified gene in A431 epidermoid carcinoma cells," *Nature*, 309, pp. 418–425 (1984).

Ullrich et al., "Isolation of the human insulin–like growth factor I gene using a single synthetic DNA probe," *The EMBO Journal*, 3, pp. 361–364 (1984).

Ullrich et al., "Human insulin receptor and its relationship to the tyrosine kinase family of oncogenes," *Nature*, 313, pp. 756–761 (1985).

Toole et al., "Molecular cloning of a cDNA encoding human antihaemophilic factor," *Nature*, 312, pp. 342–347 (1984).

Wood et al., "Expression of active human factor VIII from recombinant DNA clones," *Nature*, 312, pp. 330–336 (1984).

Derynck et al., "Human transforming growth factor–β complementary DNA sequence and expression in normal and transformed cells," *Nature*, 316, pp. 701–705 (1985).

Mason et al., "Complementary DNA sequences of ovarian follicular fluid inhibin show precursor structure and homology with transforming growth factor–β," *Nature*, 318, pp. 659–663 (1985).

Docherty et al., "Sequence of human tissue inhibitor of metalloproteinases and its identity to erythroid–potentiating activity," *Nature*, 318, pp. 66–69 (1985).

Lauffer et al., "Topology of signal recognition particle receptor in endoplasmic reticulum membrane," *Nature*, 318, pp. 334–338 (1985).

Betsholtz et al., "cDNA sequence and chromosomal localization of human platelet–derived growth factor A–chain and its expression in tumour cell lines," *Nature*, 320, pp. 695–699 (1986).

Knopf et al., "Cloning and expression of multiple protein kinase C cDNAs," *Cell*, 46, pp. 491–502 (1986).

Benedum et al., "The primary structure of bovine chromogranin A: a representative of a class of acidic secretory proteins common to a variety of peptidergic cells," *The EMBO Journal*, 5, No. 7, pp. 1495–1502 (1986).

Abraham et al., "Nucleotide sequence of a bovine clone encoding the angiogenic protein, basic fibroblast growth factor," *Science*, 233, pp. 545–548 (1986).

Ullrich et al., "Insulin–like growth factor I receptor primary structure: comparison with insulin receptor suggests structural determinants that define functional specificity," *The EMBO Journal*, 5, pp. 2503–2512 (1986).

Grundmann et al., "Characterization of cDNA coding for human factor XIIIa," *Proc. Natl. Acad. Sci. USA*, 83, pp. 8024–8028 (1986).

Bray et al., "Human cDNA clones for four species of $G_\alpha$, signal transduction protein," *Proc. Natl. Acad. Sci. USA*, 83, pp. 8893–8897 (1986).

Anderson et al., "Isolation of a genomic clone for bovine pancreatic trypsin inhibitor by using a unique–sequence synthetic DNA probe," *PNAS (USA)*, 80, pp. 6836–6840 (1983).

Church et al., "Genomic sequencing" *PNAS (USA)*, 81, pp. 1991–1995 (1984).

Souza et al., *American Society of Hematology*, Abstract 536, p. 162a, (Nov. 1985).

Neumeier et al., "Purification of granulocyte colony–stimulating factor monitored by ultrathin–layer isoelectric focusing," *2–Mammalian Hormones,* vol., 97, p. 113 (1982).

Okabe et al., "Large–scale preparation and characterization of human colony–stimulating factor," *Journal of Cellular Physiology,* 110, pp. 43–49 (1982).

Dalbadie–McFarland, G. et al., "Oligonucleotide–directed Mutagenesis as a General and Powerful Method for Studies of Protein Function," *Proc. Natl. Acad. Sci., USA,* 79:6409–6413 (Nov., 1982).

McWilliam et al., *J. Exp. Med.,* 179(4):1331–1336 (1994) (Abstract).

Nicola, N.A. et al., "Separation of Functionally Distinct Human Granulocyte–Macrophage Colony–Stimulating Factors," *Blood,* 54:614–627 (1979).

Pawinska et al., *Mater. Med. Pol.,* 23(1):13–16 (1991).

Tujsawa et al., CA, 105 (1986) (#1891929).

Souza et al., "Recombinant–human granulocyte colony–stimulating factor: effects on normal and leukemic myeloid cells," *Science,* 232:61–65 (1986).

Hartung, T. et al., "Effect of Granulocyte Colony–Stimulating Factor Treatment on Ex Vivo Blood Cytokine Response in Human Volunteers," *Blood,* 85(9):2482–2489 (1995).

Nagata, S. et al., "Gene Structure and Function of Granulocyte Colony–Stimulating Factor," *BioEssays,* 10(4):115–117 (1989).

Donahue et al., "Stimulation of haematopoiesis in primates by continuous infusion of recombinant human GM–CSF," *Nature,* 321:872–875 (1986).

Gabrilove et al., "Pluripoietin α: A second human hematopoietic colony–stimulating factor produced by the human bladder carcinoma cell line 5637," *Proc. Natl. Acad. Sci., USA,* 83:2478–2482 (1986).

Gasson et al., "Purified Human Granulocyte–Macrophage Colony–Stimulating Factor: Direct Action on Neutrophils," *Science,* 226:1339–1342 (1984).

Hogg, N., "Factor–induced differentiation and activation of macrophages," *Immunology Today,* 7(3):65–66 (1986).

Lu et al., "Effects of Recombinant Human Tumor Necrosis Factor α, Recombinant Human γ–Interferon, and Prostaglandins E on Colony–Formation of Human Hematopoietic Progenitor Cells Stimulated by Natural Human Pluripotent Colony–Stimulating Factor, Pluripoietin α, and Recombinant Erythropoietin in Serum–free Cultures," *Cancer Research,* 46:4357–4361 (1986).

Schrader et al., "Structural homologues among the hemopoietins," *Proc. Natl. Acad. Sci., USA,* 86:2458–2462 (1986).

Whettan et al., "Haemopoietic growth factors," *TIBS,* 11:207–211 (1986).

Bebbington et al., "The expression of recombinant DNA products in mammalian cells," *TIBS,* 3:314–317 (1985).

De Ferra et al., "Alternative Splicing Accounts for the Four Forms of Myelin Basic Protein," *Cell,* 43:721–727 (1985).

Dexter, T.M., "The message in the medium," *Nature,* 309:746–747 (1984).

Gabrilove et al., "Constitutive Production of Leukemia Differentiation, Colony–Stimulating, Erythroid Burst–Promoting, and Pluripoietic Factors by a Human Hepatoma Cell Line: Characterization of the Leukemia Differentiation Factor," *Blood,* 66:407–415 (1985).

Harris et al., "Distinct Differentiation–inducing Activities of γ–Interferon and Cytokine Factors Acting on the Human Promyelocytic Leukemia Cell Line HL–60," *Cancer Research,* 45:3090–3095 (1985).

Ikebuchi et al., "Granulocyte colony–stimulating factor enhances interleukin 3–dependent proliferation of multipotential hemopoietic progenitors," *Proc. Natl. Acad. Sci., USA,* 85:3445–3449 (1988).

Metcalf, D., "The Molecular Biology and Functions of the Granulocyte–Macrophage Colony–Stimulating Factors," *Blood,* 67:257–267 (1986).

Sieff et al., "Human Recombinant Granulocyte–Macrophage Colony–Stimulating Factor: A Multilineage Hematopoietin," *Science,* 230:1171–1173 (1985).

\* cited by examiner

FIG. 2A

```
                    HindIII
5' - AGCTTGGACTCAGCGGGGGGGGGGGGGGGGGGGGGGGGGGGGGGGGGG[ENNNNN]

-12                     -10                                                              -1  +1
      Leu Trp His Ser Ala Leu Trp Thr Val Gln Glu Ala Thr Pro Leu Gly Pro
      CTG TGG CAC AGT GCA CTC TGG ACA GTG CAG GAA GCC ACC CCC CTG GGC CCT
      GAC ACC GTG TCA CGT GAG ACC TGT CAC GTC CTT CGG TGG GGG GAC CCG GGA
                              HgiAI                                  ApaI
                        10                              20
      Ala Ser Leu Pro Gln Ser Phe Leu Leu Lys Cys Leu Glu Gln Val Arg Lys Ile Gln
      GCC AGC CTG CCC CAG AGC TTC CTG CTC AAG TGC TTA GAG CAA GTG AGG AAG ATC CAG
      CGG TCG GAC GGG GTC TCG AAG GAC GAG TTC ACG AAT CTC GTT CAC TCC TTC TAG GTC
                  30                              40
      Gly Asp Gly Ala Leu Gln Lys Leu Cys Ala Thr Tyr Lys Leu Cys His Pro Glu
      GGC GAT GGC GCA GCG AAG CTG TGT GCC ACC TAC AAG CTG CAC CCC GAG
      CCG CTA CCG CGT CGC TTC GAC ACA CGG TGG ATG TTC GAC GTG GGG CTC
                  50                              60
      Glu Val Leu Leu Gly His Ser Leu Gly Ile Pro Trp Ala Pro Leu Ser Ser Cys Pro
      GAG GTG CTG CTC GGA CAC TCT CTG GGC ATC CCC TGG GCT CCC CTG AGC TCG TGC CCC
      CTC CAC GAC GAG CCT GTG AGA GAC CCG TAG GGG ACC CGA GGG GAC TCG AGC ACG GGG
                  70                              80
      Ser Gln Ala Leu Gln Leu Ala Gly Cys Leu Ser Gln Leu His Ser Gly Leu Phe Tyr
      AGC CAG GCC CTG CAG CTG GCA GGC TGC TTG AGC CAA CTC CAT AGC GGC CTT TTC TAC
      TCG GTC CGG GAC GTC GAC CGT CCG ACG AAC TCG GTT GAG GTA TCG CCG GAA AAG ATG
                  90                              100
      Gln Gly Leu Leu Gln Ala Leu Glu Gly Ile Ser Pro Glu Leu Gly Pro Thr Leu Asp Thr
      CAG GGG CTC CTG CAG GCC CTG GAA GGG ATC TCC CCC GAG TTG GGT CCC ACC TTG GAC ACA
      GTC CCC GAG GAC GTC CGG GAC CTT CCC TAG AGG GGG CTC AAC CCA GGG TGG AAC CTG TGT
```

FIG. 2B

```
                                                        120
Leu Gln Leu Asp Val Ala Asp Phe Ala Thr Thr Ile Trp Gln Met Glu Glu Leu Gly
CTG CAG CTG GAC GTC GCC GAC TTT GCC ACC ACC ATC TGG CAG ATG GAA GAA CTG GGA
GAC GTC GAC CTG CAG CGG CTG AAA CGG TGG TGG TAG ACC GTC TAC CTT CTT GAC CCT 130                         140
Met Ala Pro Ala Leu Gln Pro Thr Gln Gly Ala Met Pro Ala Phe Ala Ser Ala Phe Gln
ATG GCC CCT GCC CTG CAG CCC ACC CAG GGT GCC ATG CCG GCC TTC GCC TCT GCT TTC CAG
TAC CGG GGA CGG GAC GTC GGG TGG GTC CCA CGG TAC GGC CGG AAG CGG AGA CGA AAG GTC

160
Arg Arg Ala Gly Val Leu Val Ala Ser His Leu Gln Ser Phe Leu Glu Val Ser Tyr
CGC CGG GCA GGG GTC CTG GTT GCC TCC CAT CTG CAG AGC TTC CTG GAG GTG TCG TAC
GCG GCC CGT CCC CAG GAC CAA CGG AGG GTA GAC GTC TCG AAG GAC CTC CAC AGC ATG

174
Arg Val Leu Arg His Leu Ala Gln Pro OP
CGC GTT CTA CGC CAC CTT GCC CAG CCC TGA GCC AAG CCC TCC CCA TCC CAT GTA TTT ATC
CGC CAA GAT GCG GTG GAA CGG GTC GGG ACT

TCT ATT TAA TAT TTA TGT CTA TTT AAG CCT CTG CAT TTC TGA GTT TCA TTC TCC TGC CTG TAG CAG

AGC CCC AGG CCT CTG CCT GTC CTC CCA TCC CCT GGA CTG GGA GGT AGA TAG GTA AAT ACC AAG
        StuI

TGA GAA AAA GCT CCT GTC CTC CCC AGC CCT GGC TCT GCA ATG GGC ACT GGG ATG AGC CGC

TAT TTA CTA TGA CTG CTC CCC AGG GTC CCC ACC TGG GAC CCT TGA GAG TAT CAG GTC TCC CAC

TGT GAG CCC CTG GTC CTG AGG GTC CCC ACC TGG GAC CCT TGA GAG TAT CAG GTC TCC CAC
```

FIG. 2C

```
GTG GGA GAC AAG AAA TCC CTG TTT AAT ATT TAA ACA GCA GTG TTC CCC ATC TGG GTC CTT

GCA CCC CTC ACT CTG GCC TCA GCC GAC TGC ACA GCG GCC CCT GCA TCC CCT TGG CTG TGA

GGC CCC TGG ACA AGC AGA GGT GGC CAG AGC TGG GAG GCA TGG CCC TGG GGT CCC ACG AAT

TTG CTG GGG AAT CTC GTT TTT CTT AAG ACT TTT GGG ACA TGG TTT GAC TCC CGA ACA

TCA CCG ACG TGT CTC CTG TTT TTC TGG GTG CCC TCG GGA CAC CTG CCC TGC CCC CAC GAG

GGT CAG GAC TGT GAC TCT TTT TAG GGC CAG GCA GGT GCC TGG ACA TTT GCC TTG CTG GAC
                                                              StuI
GGG GAC TGG GGA TGT GGG AGG GAG CAG ACA GGA ATC ATG TCA GGC CTG TGT GTG AAA

GGA AGC TCC ACT GTC ACC CTC TTC ACC CCC CAC TCA CCA GTG TCC CCT CCA CTG

TCA CAT TGT AAC TGA ACT TCA GGA TAA TAA AGT GTT TGC CTC CA
```

[≅150-200 base poly A plus 25-30 bases plasmid DNA preceding a PvuII restriction site]-3'

GGGGACAGGCTTGAGAATCCCAAAGGAGAGGGGCAAAGGACACTGCCCCCGCAAGTCTGCCAGAGCAGAG 70

AGGGAGACCCCGACTCAGCTGCCACTTCCCCACAGGCTCGTGCCGCTTCCAGGCGTCTATCAGCGGCTCA 140

GCCTTTGTTCAGCTGTTCTGTTCAAACACTCTGGGGCCATTCAGGCCTGGTGGGCAGCGGGAGGAAGG 210

GAGTTTGAGGGGGCAAGGCGACGTCAAAGGAGGATCAGAGATTCCACAAATTTCACAAAACTTTCGCAAA 280

CAGCTTTTTGTTCCAACCCCCCCTGCATTGTCTTGGACACCAAATTTGCATAAATCCTGGAAGTTATTAC 350

TAAGCCTTAGTCGTGGCCCCAGGTAATTTCCTCCCAGGCCTCCATGGGGTTATGTATAAAGGGCCCCTA 420
                                                                  -30
                                                          MetAlaGlyProAlaThr
GAGCTGGGCCCCAAAACAGCCCGGAGCCCTGCAGCCCCACCCAGACCCATGGCTGGACCCTGCCACC 490
GlnSerProMetLysLeuMetA
         -20       -18
CAGAGCCCCATGAAGCTGATGGGTGAGTGTCTTGGCCCTGGAGAGCCGCCTGCATGGGA 560

GGGAGGCTGTGTGACAGAGGGGCTGGGGATCCCCGTTCTGGGAATGGGGATTAAAGGCACCCAGTGTCC 630
                                                              -16
                                                          laLeuGlnLeuL
CCGAGAGGGCCTCAGTGGTAGGGAACAGCATGTCTCCTGAGCCCGCTCTGTCCCAGCCCTGCAGCTGC 700

FIG. 3A

```
                    -1  +1
euLeuTrpHisSerAlaAlaLeuTrpThrProLeuGlyProAlaSerSerLeuProGl
                                                         10
TGCTGTGGGCACAGTGCACTCTGGACAGTGCAGGAAGCCACCCCTGGGCCCTGCCAGTCCCCTGCCCA    770
        20                                  30
nSerPheLeuLeuLysCysLeuLysGluGlnValArgLysIleGlnGlyAspGlyAlaAlaLeuGlnLeuLys
GAGCTTCCTGCTCAAGTGCTTAGAGCAAGTGAGGAAGATCCAGGGCGATGGCGCAGCGCTCCAGGAGAAG    840
35
Leu
CTGGTGAGTGAGGTGGGTGAGAGGGCTGTGGAGGGAAGCCCGGTGGGGAGAGCTAAGGGGATGGAACTG    910

CAGGGCCAACATCCTCTGAAGGGACATGGGAGAGAATATTAGGAGCAGTGCTCGGGAGGGCTGGCTGGGG    980

GGACTTGGGGAGGAGGACCCTTGGTGGGGACAGTGTGAGATCAGAGACCAGAGAGTGGGGGTGCAGGGC    1050

ACATTCAGGAGAAAGGGCAAGGGGAGGAGGAAAGACCAGAGAGTCGGGGAGGACCCGGGAAGGAGGCATC    1120

CAGCCTGGCAGGACATGGAGGGGAGGAAGGAGACCCGGGAAGGAGGCGGGACC    1190
                                       36
                                       CysAlaThrTyrLysLeuCysHisProGlu
CGGCCACGGGCGAGTCTCACTCAGCATCCTTCCATCCCCAGTGTGCCACCTACAAGCTGTGCCACCCCGAG    1260
          50                                       60
GluLeuValLeuLeuGlyHisSerLeuGlyIleProTrpAlaProLeuSerSerCysProSerGlnAlaL
GAGCTGGTGCTGCTCGGACACTCTCTGGGCATCCCCCTGGCTCCCCTGAGCAGCTGCCCCAGCCAGGCCC    1330
```

```
         160                                         170                            174
alaAlaSerHisLeuGlnSerPheLeuGluValSerTyrArgValLeuArgHisLeuAlaGlnProOP
TTGCCTCCCATCTGCAGAGCTTCCTGGAGGTGTCGTACCGCGTTCTACGCCACCTGCCCAGCCCTGAGC       1960

CAAGCCCTCCCCATCCCATGTATTTATCTCTATTTAATATTTATGTCTATTTAAGCCTCATATTTAAAGA       2030

CAGGGAAGAGCAGAACGGAGCCCCAGGCCCTCTGTCCTTCCCTGCATTTCTGAGTTTCATTCTCCTGCC       2100

TGTAGCAGTGAGAAAAAGCTCCTGTCCTCCCCATCCCCCTGGACTGGGAGGTAGATAGGTAAATACCAAGTA    2170

TTTATTACTATGACTGCTCCCCAGCCCTGGCTCTGCAATGGGCACTGGATGAGCCGCTGTGAGCCCCTG       2240

GTCCTGAGGGTCCCCACCTGGGACCCCTTGAGAGTATCAGGTCTCCCACGTGGGAGACAAGAAATCCCTGT    2310

TTAATATTTAAACAGCAGTGTTCCCCATCTGGGTCCTTGCACCCCTCACTCTGGCCCTCAGCCGACTGCAC    2380

AGCGGGCCCCTGCATCCCCCTTGGCTGTGAGGCCCCTGGACAAGCAGAGGTGGCCAGAGCTGGGAGGCATGG   2450

CCCTGGGGTCCCACGAATTTGCTGGGGAATCTCGTTTCTTCTTAAGACTTTTGGGACATGGTTTGACT       2520

CCCGAACATCACCGACGTGTCTCCTGTTTTCTGGGTGGCCCTCGGGACACCTGCCCCCACGAGGG           2590
```

FIG. 3D

TCAGGACTGTGACTCTTTTAGGGCCAGGCCAGGTGCCTGGACATTTGCCTTGCTGGATGGGGACTGGGGA 2660

TGTGGGAGGGAGCAGACAGGAGGAATCATGTCAGGCCTGTGTGTGAAAGGAAGCTCCACTGTCACCCTCC 2730

ACCTCTTCACCCCCCACTCACCAGTGTCCCCCTCCACTGTCACATTGTAACTGAACTTCAGGATAATAAAG 2800

TGTTTGCCTCCAGTCACGTCTCCTTCCTCCTTCTTGAGTCCAGCTGGTGCCTGGCCAGGGGCTGGGGAGGTG 2870

GCTGAAGGGTGGGAGAGGCCAGAGGGAGGAGGTCGGGGAGGAGGAGGTCCAGGGAGGAGGAGGAGG 2940

AAAGTTCTCAAGTTCGTCTGACATTCATTCCGTTAGCACATATTTATCTGAGCACCTACTCTGTGCAGAC 3010

GCTGGGCTAAGTGCTGGGACACAGCAGGAACAAGGCAGACATGGAATCTGCACTCGAG 3070

EChpG-CSFDNA SECTION I

```
         10         1         20                    30                    40        2         50                       60
    CTAGAAAAA ACCAAGGAGG TAATAAATAA TGACTCCATT AGGTCCTGCT TCTTCTCTGC
            TTTTT TGGTTCCTCC ATTATTTATT ACTGAGGTAA TCCAGGACGA AGAAGAGACG
                        8                                              9
    XbaI 70        3         80                    90                   100        4        110                      120
    CGCAAAGCTT TCTGCTGAAA TGTCTGCAAC AGGTTCGTAA AATCCAGGGT GACGGTGCTG
            GCGTTTCGAA AGACGACTTT ACAGACGTTG TCCAAGCATT TTAGGTCCCA CTGCCACGAC
                       10                                             11

130        5        140                   150        6        160                   170                      180
    CACTGCAAGA AAAACTGTGC GCTACTTACA AACTGTGCCA TCCGGAAGAG CTGGTACTGC
            GTGACGTTCT TTTTGACACG CGATGAATGT TTGACACGGT AGGCCTTCTG GACCATGACG
                       12                                             13

7       190                   100
    TGGGTCATTC TCTTGG
            ACCCAGTAAG AGAACCCTAG
                       14
                               BamHI
```

FIG. 5

EChpG-CSFDNA SECTION II

```
         10        15   20             30             16   40         16   50             60
GATCCCGTG GGCTCCGCTG TCTTCTTGTC CATCTCCAAGC TCTTTCAGCTG GCTGGTTGTC
         CCGAGGCGAC AGAAGAACAG GTAGAGTTCG AGAAGTCGAC CGACCAACAG
         GGCAC                                      24
BamHI    23

70   17   80             90        18  100            110        19  120
TGTCTCAACT GCATTCTGGT CTGTTCCTGT ATCAGGGTCT TCTGCAAGCT CTGGAAGGTA
ACAGAGTTGA CGTAAGACCA GACAAGGACA TAGTCCCAGA AGACGTTCGA GACCTTCCAT
         25                      26                             27

130        140       20  150            160            21  170            180
TCTCTCCCGA ACTGGGTCCG ACTCTGGACA CTCTGCAGCT AGATGTAGCT GACTTTGCTA
AGAGAGGCCT TGACCCAGGC TGAGACCTGT GAGACGTCGA TCTACATCGA CTGAAACGAT
                                28                                          29

190        200        22 210
CTACTATTTG GCAACAGATG GAAGAGCTCA AAG
GATGATAAAC CGTTGTCTAC CTTCTCGAGT TTCTTAA
                                30
                      SstI      EcoRI
```

FIG. 6

EChpG-CSFDNA SECTION III

```
          10        31    20              30         40        32    50              60
     GATCCAAAG AGCTGGGTAT GGCACCAGCT CTGCAACCGA CTCAAGGTGC TATGCCGGCA
          GTTTC TCGAGCCATA CCGTGGTCGA GACGTTGGCT GAGTTCCACG ATACGGGCCT
     BamHI        SstI                                         38
                            37

70    33    80              90        100        34   110             120
     TTCGCTTCTG CATTCCAGCG TCGTGCAGGA GGTGTACTGG TTGCTTCTCA TCTGCAATCT
     AAGCGAAGAC GTAAGGTCGC AGCACGTCCT CCACATGACC AACGAAGAGT AGACGTTAGA
                     39                                        40

35   130             140        150        36   160             170
     TTCCTGGAAC TATCTTACCG TGTTCTGCGT CATCTGGCTC AGCCGTAATA G
     AAGGACCTTG ATAGAATGGC ACAAGACGCA GTAGACCGAG TCGGCATTAT CTTAA
              41                                        42              EcoRI
```

FIG. 7A

```
                                                   -1  +1
                                                   Met Thr Pro Leu Gly Pro Ala Ser Ser Leu
C   TAG AAA AAA CCA AGG AGG TAA ATA ACT CCA TTA GGT CCT GCT TCT TCT CTG
                                               20
CCG CAA AGC TTT CTG CTG AAA TGT CTG GAA CAG GTT CGT AAA ATC CAG GGT GAC GGT GCT
Pro Gln Ser Phe Leu Leu Lys Cys Leu Glu Gln Val Arg Lys Ile Gln Gly Asp Gly Ala
                                               40
GCA CTG CAA GAA AAA CTG TGC CAT CCG GAA GAG CTG GTA CTG
Ala Leu Gln Glu Lys Leu Cys His Pro Glu Glu Leu Val Leu
        30                                     40
GCA CTG CAA GAA AAA CTG TGC CAT CCG GAA GAG CTG GTA CTG
Ala Leu Gln Glu Lys Leu Cys His Pro Glu Glu Leu Val Leu
        50                                     60
CTG GGT CAT TCT CTT GGG ATC CCG TGG GCT CCG CTG TCT TCT TGT CCA TCT CAA GCT CTT
Leu Gly His Ser Leu Gly Ile Pro Trp ala Pro Leu Ser Ser Cys Pro Ser Gln Ala Leu
        70                                     80
CAG CTG CTG GCT GGT TGT CTG CTG TCT CAA CTG CAT CTG GGT CTG TAT CAG GGT CTT CTG
Gln Leu Leu Ala Gly Cys Leu Leu Ser Gln leu His Ser Gly Leu Phe Leu Tyr Gln Gly Leu Leu
        90                                     100
CAA GCT CTG GAA GGT ATC TCT CCG GAA CTG GGT CCG ACT CTG GAC ACT CTG CAG CTA GAT
Gln Ala Leu Glu Gly Ile Ser Pro Glu Leu Gly Pro Thr Leu Asp Thr Leu Gln Leu Asp
        110                                    120
GTA GCT GAC TTT GCT ACT ACT ATT TGG CAA CAG ATG GAA GAG CTC GGT ATG GCA CCA GCT
Val Ala Asp Phe Ala Thr Thr Ile Trp Gln Gln Met Glu Glu leu Gly Met Ala Pro Ala
        130                                    140
CTG CAA CCG ACT CAA GGT GCT ATG CCG GCA TTC GCA TCT GCA TTC CAG CGT CGT GCA GGA
Leu Gln Pro Thr Gln Gly Ala Met Pro Ala Phe Ala Ser Ala Phe Gln Arg Arg Ala Gly
```

FIG. 7B

```
150
Gly Val Leu Val Ala Ser His Leu Gln Ser Phe Leu Glu Val Ser Tyr Arg Val Leu Arg
GGT GTA CTG GTT GCT TCT CAT CTG CAA TCT TTC CTG GAA GTA TCT TAC CGT GTT CTG CGT
                                    160

170                 174
His Leu Ala Gln Pro
CAT CTG GCT CAG CCG TAA TAG CCG TAA TAG AAT T
```

(Note: portion after 174 reads: CAT CTG GCT CAG CCG TAA TAG AAT T)

FIG. 8

```
1   ATCGATTTGATTCTAGAAGGAGGAATAACATATGGTTAACGCGTTGGAATTCGGTACCAT
    TAGCTAAACTAAGATCTTCCTCCTTATTGTATACCAATTGCGCAACCTTAAGCCATGGTA

1 ClaI, 12 XbaI, 29 NdeI, 35 HincII, HpaI, 39 MluI, 47 EcoRI,
    53 HgiCI KpnI, 57 NcoI StyI, 61  GGAAGCTTACTCGAGGATCCCGGGATAAATAAGTAACGATCC
    CCTTCGAATGAGCTCCTAGGGCCCTATTTATTCATTGCTAGG 63 HindIII, 70 AvaI XhoI, 75 BamHI Xho2, 79 Sac2,
```

| Competitor | (U/ml) | WEHI-3B (D⁺) cpm | % Inhib. | ANLL (M4) cpm | % Inhib. | ANLL (M5B) cpm | % Inhib. |
|---|---|---|---|---|---|---|---|
| Exp. 1 | | | | | | | |
| none | 0 | 6,608 | - | 1,218 | - | 122 | - |
| natural hpG-CSF: | 10,000 | 685 | 90 | | | | |
| | 2,000 | 1,692 | 74 | 34 | 97 | -376 | 0 |
| | 200 | 2,031 | 69 | | | | |
| rhpG-CSF: | 10,000 | 0 | 100 | | | | |
| | 2,000 | 1,185 | 82 | 202 | 83 | 0 | 0 |
| | 200 | 2,330 | 65 | | | | |
| Exp. 2 | | | | | | | |
| none | 0 | 2,910 | 0 | | | | |
| natural hpG-CSF: | 2,000 | 628 | 78 | | | | |
| GM-CSF: | 2,000 | 3,311 | 0 | | | | |

FIG. 9

PHARMACEUTICAL COMPOSITIONS COMPRISING PLURIPOTENT GRANULOCYTE COLONY-STIMULATING FACTOR

This is a continuation of U.S. application Ser. No. 09/060,275, filed Apr. 14, 1998 now U.S. Pat. No. 6,004,548, in turn a divisional of U.S. application Ser. No. 08/679,897, filed Jul. 15, 1996 now U.S. Pat. No. 5,830,705; in turn a continuation of U.S. Ser. No. 08/452,135, filed May 26, 1995 now U.S. Pat. No. 5,582,823; in turn a divisional of 08/243,556 filed May 16, 1994 now abandoned; in turn a File Wrapper Continuation of 08/065,465 filed May 20, 1993 now abandoned; in turn a File Wrapper Continuation of 07/269,885 filed Nov. 10, 1988 now abandoned; in turn a divisional of 06/835,548 filed Mar. 3, 1986 now U.S. Pat. No. 4,810,643; in turn a continuation-in-part of 06/768,959 filed Aug. 23, 1985 now abandoned.

BACKGROUND

The present invention pertains in general to hematopoietic growth factors and to polynucleotides encoding such factors. The present application pertains in particular to mammalian pluripotent colony stimulating factors, specifically human pluripotent granulocyte colony-stimulating factor (hpG-CSF), to fragments and polypeptide analogs thereof and to polynucleotides encoding the same.

The human blood-forming (hematopoietic) system replaces a variety of white blood cells (including neutrophils, macrophages, and basophils/mast cells), red blood cells (erythrocytes) and clot-forming cells (megakaryocytes/platelets). The hematopoietic system of the average human male has been estimated to produce on the order of $4.5 \times 10^{11}$ granulocytes and erythrocytes every year, which is equivalent to an annual replacement of total body weight. Dexter et al., *BioEssays*, 2, 154–158 (1985).

It is believed that small amounts of certain hematopoietic growth factors account for the differentiation of a small number of progenitor "stem cells" into the variety of blood cell lines, for the tremendous proliferation of those lines, and for the ultimate differentiation of mature blood cells from those lines. Because the hematopoietic growth factors are present in extremely small amounts, the detection and identification of these factors has relied upon an array of assays which as yet only distinguish among the different factors on the basis of stimulative effects on cultured cells under artificial conditions. As a result, a large number of names have been coined to denote a much smaller number of factors. As an example of the resultant confusion the terms, IL-3, BPA, multi-CSF, HCGF, MCGF and PSF are all acronyms which are now believed to apply to a single murine hematopoietic growth factor. Metcalf, *Science*, 229, 16–22 (1985). See also, Burgess, et al. *J.Biol.Chem.*, 252, 1998–2003 (1977), Das, et al. *Blood*, 58, 630–641 (1981), Ihle, et al., *J.Immunol.*, 129, 2431 (1982), Nicola, et al., *J.Biol.Chem.*, 258, 9017 (1983), Metcalf, et al., *Int.J.Cancer*, 30, 773 (1982), and Burgess, et al. *Int.J.Cancer*, 26, 647 (1980), relating to various murine growth regulatory glycoproteins.

The application of recombinant genetic techniques has brought some order out of this chaos. For example, the amino acid and DNA sequences for human erythropoietin, which stimulates the production of erythrocytes, have been obtained. (See, Lin, PCT Published Application No. 85/02610, published Jun. 20, 1985.) Recombinant methods have also been applied to the isolation of cDNA for a human granulocyte-macrophage colony-stimulating factor. See, Lee, et al., *Proc. Natl. Acad. Sci. (USA)*, 82, 4360–4364 (1985) and Wong, et al., *Science*, 228, 810–814 (1985). See also Yokota, et al. *Proc. Natl. Acad. Sci. (USA)*, 81, 1070 (1984), Fung, et al., *Nature*, 307, 233 (1984), and Gough, et al., *Nature*, 309, 763 (1984) relating to cloning of murine genes, as well as Kawasaki, et al., *Science*, 230, 291 (1985) relating to human M-CSF.

A human hematopoietic growth factor, called human pluripotent colony-stimulating factor (hpCSF) or pluripoietin, has been shown to be present in the culture medium of a human bladder carcinoma cell line denominated 5637 and deposited under restrictive conditions with the American Type Culture Collection, Rockville, Md. as A.T.C.C. Deposit No. HTB-9. The hpCSF purified from this cell line has been reported to stimulate proliferation and differentiation of pluri-potent progenitor cells leading to the production of all major blood cell types in assays using human bone marrow progenitor cells. Welte et al., *Proc. Natl. Acad. Sci. (USA)*, 82, 1526–1530 (1985). Purification of hpCSF employed: $(NH_4)_2SO_4$ precipitation; anion exchange chromatography (DEAE cellulose, DE52); gel filtration (AcA54 column); and C18 reverse phase high performance liquid chromatography. A protein identified as hpCSF, which is eluted in the second of two peaks of activity in C18 reverse phase HPLC fractions, was reported to have a molecular weight (MW) of 18,000 as determined by sodium dodecyl sulphate (SDS)-polyacrylamide gel electrophoresis (PAGE) employing silver staining. HpCSF was earlier reported to have an isoelectric point of 5.5 [Welte, et al., *J. Cell. Biochem.*, Supp 9A, 116 (1985)] and a high differentiation activity for the mouse myelo-monocytic leukemic cell line WEHI-3B D$^+$ [Welte, et al., UCLA Symposia on Molecular and Cellular Biology, Gale, et al., eds., *New Series*, 28 (1985)]. Preliminary studies indicate that the factor identified as hpCSF has predominantly granulocyte colony-stimulating activity during the first seven days in a human CFU-GM assay.

Another factor, designated human CSF-β, has also been isolated from human bladder carcinoma cell line 5637 and has been described as a competitor of murine $^{125}$I-labelled granulocyte colony-stimulating factor (G-CSF) for binding to WEHI-3B D$^+$ cells in a dose-response relationship identical to that of unlabelled murine G-CSF [Nicola, et al., *Nature*, 314, 625–628 (1985)]. This dose-response relationship had previously been reported to be unique to unlabelled murine G-CSF and not possessed by such factors as M-CSF, GM-CSF, or multi-CSF [Nicola, et al., *Proc. Natl. Acad. Sci. (USA)*, 81, 3765–3769 (1984)]. CSF-β and G-CSF are also unique among CSF's in that they share a high degree of ability to induce differentiation of WEHI-3B D$^+$ cells. Nicola, et al., *Immunology Today*, 5, 76–80 (1984). At high concentrations, G-CSF stimulates mixed granulocyte/macrophage colony-forming cells [Nicola, et al., (1984) supra], which is consistent with preliminary results indicating the appearance of granulocytic, monocytic, mixed granulocytic/monocytic and eosinophilic colonies (CFU-GEMM) after 14 days incubation of human bone marrow cultures with hpCSF. CSF-β has also been described as stimulating formation of neutrophilic granulocytic colonies in assays which employed mouse bone marrow cells, a property which has been a criterion for identification of a factor as a G-CSF. On the basis of these similarities, human CSF-β has been identified with G-CSF (granulocytic colony stimulating factor). Nicola et al., *Nature*, 314, 625–628 (1985).

Based upon their common properties, it appears that human CSF-β of Nicola, et al., supra, and the hpCSF of Welte, et al., supra, are the same factor which could properly be referred to as a human pluripotent granulocyte colony-stimulating factor (hpG-CSF). Characterization and recombinant production of hpG-CSF would be particularly desirable in view of the reported ability of murine G-CSF to completely suppress an in vitro WEHI-3B D+ leukemic cell population at "quite normal concentrations", and the reported ability of crude, injected preparations of murine G-CSF to suppress established transplanted myeloid leukemias in mice. Metcalf, *Science*, 229, 16–22 (1985). See also, Sachs, *Scientific American*, 284(1), 40–47 (1986).

To the extent that hpG-CSF may prove to be therapeutically significant and hence need to be available in commercial scale quantities, isolation from cell cultures is unlikely to provide an adequate source of material. It is noteworthy, for example, that restrictions appear to exist against commercial use of Human Tumor Bank cells such as the human bladder carcinoma cell line 5637 (A.T.C.C. HTB9) which have been reported as sources of natural hpCSF isolates in Welte, et al. (1985, supra).

SUMMARY OF THE INVENTION

According to the present invention, DNA sequences coding for all or part of hpG-CSF are provided. Such sequences may include: the incorporation of codons "preferred" for expression by selected nonmammalian hosts; the provision of sites for cleavage by restriction endonuclease enzymes; and the provision of additional initial, terminal or intermediate DNA sequences which facilitate construction of readily expressed vectors. The present invention also provides DNA sequences coding for microbial expression of polypeptide analogs or derivatives of hpG-CSF which differ from naturally-occurring forms in terms of the identity or location of one or more amino acid residues (i.e., deletion analogs containing less than all of the residues specified for hpG-CSF; substitution analogs, such as [Ser$^{17}$]hpG-CSF, wherein one or more residues specified are replaced by other residues; and addition analogs wherein one or more amino acid residues is added to a terminal or medial portion of the polypeptide) and which share some or all the properties of naturally-occurring forms.

Novel DNA sequences of the invention include sequences useful in securing expression in procaryotic or eucaryotic host cells of polypeptide products having at least a part of the primary structural conformation and one or more of the biological properties of naturally occurring pluripotent granulocyte colony-stimulating factor. DNA sequences of the invention are specifically seen to comprise: (a) the DNA sequence set forth in FIG. 2 and FIG. 3 or their complementary strands; (b) a DNA sequence which hybridizes (under hybridization conditions such as illustrated herein or more stringent conditions) to the DNA sequences in FIG. 2 or to fragments thereof; and (c) a DNA sequence which, but for the degeneracy of the genetic code, would hybridize to the DNA sequence in FIG. 2. Specifically comprehended in part (b) are genomic DNA sequences encoding allelic variant forms of hpG-CSF and/or encoding other mammalian species of pluripotent granulocyte colony-stimulating factor. Specifically comprehended by part (c) are manufactured DNA sequences encoding hpG-CSF, fragments of hpG-CSF and analogs of hpG-CSF which DNA sequences may incorporate codons facilitating translation messenger RNA in microbial hosts. Such manufactured sequences may readily be constructed according to the methods of Alton, et al., PCT published application WO 83/04053.

Also comprehended by the present invention is that class of polypeptides coded for by portions of the DNA complement to the top strand human cDNA or genomic DNA sequences of FIGS. 2 or 3 herein, i.e., "complementary inverted proteins" as described by Tramontano, et al., *Nucleic Acids Res.*, 12, 5049–5059 (1984).

The present invention provides purified and isolated polypeptide products having part or all of the primary structural conformation (i.e., continuous sequence of am no acid residues) and one or more of the biological properties (e.g., immunological properties and in vitro biological activity) and physical properties (e.g., molecular weight) of naturally-occurring hpG-CSF including allelic variants thereof. These polypeptides are also characterized by being the product of chemical synthetic procedures or of procaryotic or eucaryotic host expression (e.g., by bacterial, yeast, higher plant, insect and mammalian cells in culture) of exogenous DNA sequences obtained by genomic or cDNA cloning or by gene synthesis. The products of typical yeast (e.g., *Saccaromyces cerevisiae*) or procaryote [e.g., *Escherichia coli* (*E. coli*)] host cells are free of association with any mammalian proteins. The products of microbial expression in vertebrate (e.g., non-human mammalian and avian) cells are free of association with any human proteins. Depending upon the host employed, polypeptides of the invention may be glycosylated with mammalian or other eucaryotic carbohydrates or may be non-glycosylated. Polypeptides of the invention may also include an initial methionine amino acid residue (at position −1).

Also comprehended by the invention are pharmaceutical compositions comprising effective amounts of polypeptide products of the invention together with suitable diluents, adjuvants and/or carriers useful in hpG-CSF therapy.

Polypeptide products of the invention may be "labelled" by association with a detectable marker substance (e.g., radiolabelled with $^{125}$I) to provide reagents useful in detection and quantification of human hpG-CSF in solid tissue and fluid samples such as blood or urine. DNA products of the invention may also be labelled with detectable markers (such as radiolabels and non-isotopic labels such as biotin) and employed in DNA hybridization processes to locate the human hpG-CSF gene position and/or the position of any related gene family in a chromosomal map. They may also be used for identifying human hpG-CSF gene disorders at the DNA level and used as gene markers for identifying neighboring genes and their disorders.

Polypeptide products of the present invention may be useful, alone or in combination with other hematopoietic factors or drugs in the treatment of hematopoietic disorders, such as aplastic anemia. They may also be useful in the treatment of hematopoietic deficits arising from chemotherapy or from radiation therapy. The success of bone marrow transplantation, for example, may be enhanced by application of hpG-CSF. Wound healing burn treatment and the treatment of bacterial inflammation may also benefit from the application of hpG-CSF. In addition, hpG-CSF may also be useful in the treatment of leukemia based upon a reported ability to differentiate leukemic cells. Welte, et al., *Proc. Natl. Acad. Sci.* (*USA*), 82, 1526–1530 (1985) and Sachs, supra.

Numerous aspects and advantages of the invention will be apparent to those skilled in the art upon consideration of the following detailed description which provides illustrations of the practice of the invention in its presently preferred embodiments.

BRIEF DESCRIPTION OF THE DRAWINGS

FIGS. 2 through 10 are DNA sequences according to the invention.

DETAILED DESCRIPTION

Figure 1:
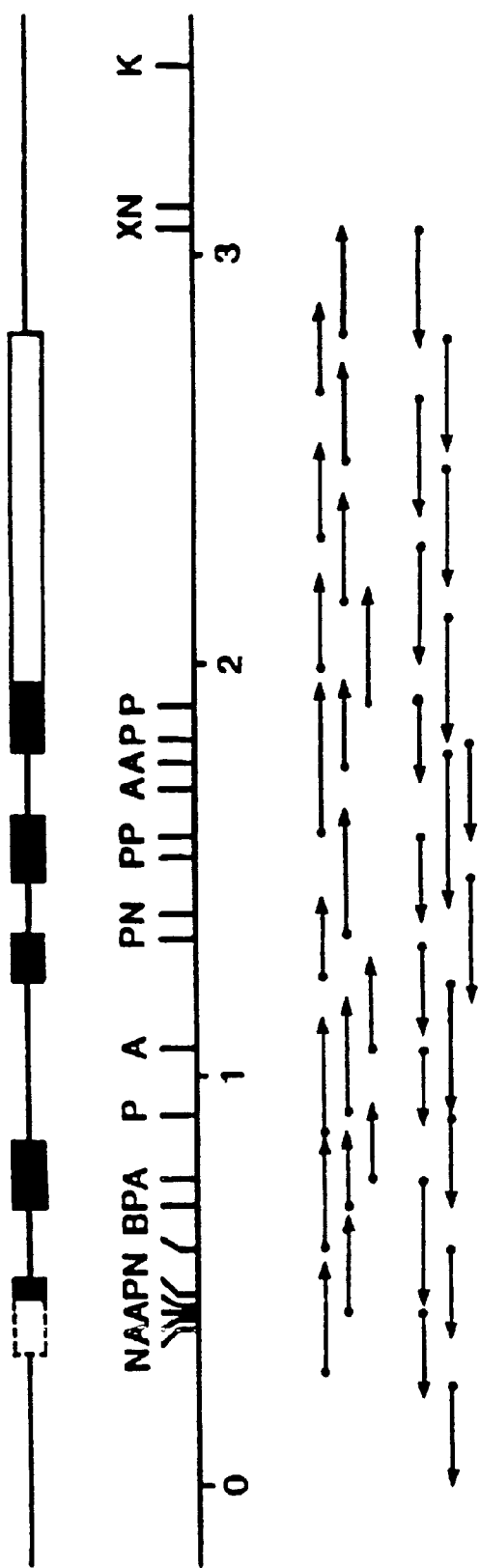
FIG. 1 is a partial restriction endonuclease map of the hpG-CSF gene accompanied by arrows depicting the sequencing strategy used to obtain the genomic sequence.

According to the present invention, DNA sequences encoding part or all of the polypeptide sequence of hpG-CSF have been isolated and characterized.

The following examples are presented by way of illustration of the invention and are specifically directed to procedures carried out prior to identification of hpG-CSF cDNA and genomic clones, to procedures resulting in such identification, and to the sequencing, development of expression systems based on cDNA, genomic and manufactured genes and verification of expression hpG-CSF and analog products in such systems.

More particularly, Example 1 is directed to amino acid sequencing of hpG-CSF. Example 2 is directed to the preparation of a cDNA library for colony hybridization screening. Example 3 relates to construction of hybridization probes. Example 4 relates to hybridization screening, identification of positive clones, DNA sequencing of a positive cDNA clone and the generation of polypeptide primary structural conformation (amino acid sequence) information. Example 5 is directed to the identification and sequencing of a genomic clone encoding hpG-CSF. Example 6 is directed to the construction of a manufactured gene encoding hpG-CSF wherein E. coli preference codons are employed.

Example 7 is directed to procedures for construction of an E. coli transformation vector incorporating hpG-CSF-encoding DNA, the use of the vector in procaryotic expression of hpG-CSF, and to analysis of properties of recombinant products of the invention. Example 8 is directed to procedures for generating analogs of hpG-CSF wherein cysteine residues are replaced by another suitable amino acid residue by means of mutagenesis performed on DNA encoding hpG-CSF. Example 9 is directed to procedures for the construction of a vector incorporating hpG-CSF analog-encoding DNA derived from a positive cDNA clone, the use of the vector for transfection of COS-1 cells, and the cultured growth of the transfected cells. Example 10 relates to physical and biological properties or recombinant polypeptide products of the invention.

EXAMPLE 1

(A) Sequencing of Material Provided By Literature Methods

A sample (3–4 µg, 85–90% pure of SDS, silver stain-PAGE) of hpG-CSF was obtained from Sloan Kettering Institute, New York, N.Y., as isolated and purified according to Welte, et al., *Proc. Natl. Acad. Sci.* (*USA*), 82, 1526–1530 (1985).

The N-terminal amino acid sequence of this sample of hpG-CSF was determined in a Run #1 by microsequence analysis using an AB407A gas phase sequencer (Applied Biosystems, Foster City, Calif.) to provide the sequence information set out in Table I below. In Tables I–IV single letter codes are employed, "X" designates a residue which was not unambiguously determined and residues in parentheses were only alternatively or tentatively assigned.

TABLE I

| 1 | 5 | 10 | 15 |
|---|---|---|---|
| K-P-L-G-P-A-S-K-L-K-Q-(G,V,S)-G-L-X-X-X | | | |

A high background was present in every cycle of the run for which results are reported in Table I, indicating that the sample had many contaminating components, probably in the form of chemical residues from purification. The sequence was retained only for reference use.

In Run #2, a second sample (5–6 µg, ~95% pure) was obtained from Sloan Kettering as for Run #1 and a sequencing procedure was performed as for Run #1. This sample was from the same lot of material employed to generate FIG. 4 of Welte, et al., *Proc. Natl. Acad. Sci.* (*USA*), 82, 1526–1530 (1985). The results are given in Table II.

TABLE II

| 1 | 5 | 10 | 15 | 20 |
|---|---|---|---|---|
| T-P-L-G-P-A-S-(S)-L-P-Q-$^{(S)}_X$-M$^{(L)}_{(M)}$-X-K-(R)-X-X-(R)-(L)-X- | | | | |

Although more residues were identified, Run #2 did not provide a sufficiently long, unambiguous sequence from which a reasonable number of probes could be constructed to search for hpG-CSF DNA. It was calculated that at least 1536 probes would have been required to attempt isolation of cDNA based on the sequence of Table II. Again, contamination of the sample was believed to be the problem.

Accordingly, a third sample (3–5 µg, ~40% pure) was obtained from Sloan Kettering as above. This preparation was electroblotted after separation by SDS-PAGE in an attempt at further purification. Sequence analysis of this sample yielded no data.

(B) Sequencing of Materials Provided by Revised Methods

In order to obtain a sufficient amount of pure material to perform suitably definitive amino acid sequence analysis, cells of a bladder carcinoma cell line 5637 (subclone 1A6) as produced at Sloan-Kettering were obtained from Dr. E. Platzer. Cells were initially cultured in Iscove's medium (GIBCO, Grand Island, N.Y.) in flasks to confluence. When confluent, the cultures were trypsinized and seeded into roller bottles (1½ flasks/bottle) each containing 25 ml of preconditioned Iscove's medium under 5% $CO_2$. The cells were grown overnight at 37° C. at 0.3 rpm.

Cytodex-1 beads (Pharmacia, Uppsala, Sweden) were washed and sterilized using the following procedures. Eight grams of beads were introduced into a bottle and 400 ml of PBS was added. Beads were suspended by swirling gently for 3 hours. After allowing the beads to settle, the PBS was drawn off, the beads were rinsed in PBS and fresh PBS was added. The beads were autoclaved for 15 minutes. Prior to use, the beads were washed in Iscove's medium plus 10% fetal calf serum (FCS) before adding fresh medium plus 10% FCS to obtain treated beads.

After removing all but 30 ml of the medium from each roller bottle, 30 ml of fresh medium plus 10% FCS and 40 ml of treated beads were added to the bottles. The bottles were gassed with 5% $CO_2$ and all bubbles were removed by suction. The bottles were placed in roller racks at 3 rpm for ½ hour before reducing the speed to 0.3 rpm. After 3 hours, an additional flask was trypsinized and added to each roller bottle containing beads.

At 40% to 50% of confluence the roller bottle cultures were washed with 50 ml PBS and rolled for 10 min. before removing the PBS. The cells were cultured for 48 hours in medium A [Iscove's medium containing 0.2% FCS, $10^{-8}$M hydrocortisone, 2 mM glutamine, 100 units/ml penicillin, and 100 μg/ml streptomycin]. Next, the culture supernatant was harvested by centrifugation at 3000 rpm for 15 min., and stored at −70° C. The cultures were refed with medium A containing 10% FCS and were cultured for 48 hours. After discarding the medium, the cells were washed with PBS as above and cultured for 48 hours in medium A. The supernatant was again harvested and treated as previously described.

Approximately 30 liters of medium conditioned by 1A6 cells were concentrated to about 2 liters on a Millipore Pellicon unit equipped with 2 cassettes having 10,000 M. W. cutoffs at a filtrate rate of about 200 ml/min. and at a retentate rate of about 1000 ml/min. The concentrate was diafiltered with about 10 liters of 50 mM Tris (pH 7.8) using the same apparatus and same flow rates. The diafiltered concentrate was loaded at 40 ml/min. onto a 1 liter DE cellulose column equilibrated in 50 mM Tris (pH 7.8). After loading, the column was washed at the same rate with 1 liter of 50 mM Tris (pH 7.8) and then with 2 liters of 50 mM Tris (pH 7.8) with 50 mM NaCl. The column was then sequentially eluted with six 1 liter solutions of 50 mM Tris (pH 7.5) containing the following concentrations of NaCl: 75 mM; 100 mM; 125 mM; 150 mM; 200 mM; and 300 mM. Fractions (50 ml) were collected, and active fractions were pooled and concentrated to 65 ml on an Amicon ultrafiltration stirred cell unit equipped with a YM5 membrane. This concentrate was loaded onto a 2 liter AcA54 gel filtration column equilibrated in PBS. The column was run at 80 ml/hr. and 10 ml fractions were collected. Active fractions were pooled and loaded directly onto a C4 high performance liquid chromatography (HPLC) column.

Samples, ranging in volume from 125 ml to 850 ml and containing 1–8 mg of protein, about 10% of which was hpG-CSF, were loaded onto the column at a flow rate ranging from 1 ml to 4 ml per minute. After loading and an initial washing with 0.12 M ammonium acetate (pH 6.0–7.0) in 80% 2-propanol at a flow rate of 1/ml/min,one. One milliliter fractions were collected and monitored for proteins at 220 nm, 260 nm and 280 nm.

As a result of purification, fractions containing hpG-CSF were clearly separated (as fractions 72 and 73 of 80) from other protein-containing fractions. hpG-CSF was isolated (150–300 μg) at a purity of about 85±5% and at a yield of about 50%. From this purified material 9 μg was used in Run #4, an amino acid sequence analysis wherein the protein sample was applied to a TFA-activated glass fiber disc without polybrene. Sequence analysis was carried out with an AB 470A sequencer according to the methods of Hewick, et al., *J. Biol. Chem.*, 256, 7990–7997 (1981) and Lai, *Anal. Chim. Acta*, 163, 243–248 (1984). The results of Run #4 appear in Table III.

TABLE III

```
    1                   5                    10
    Thr-Pro-Leu-Gly-Pro-Ala-Ser-Ser-Leu-Pro-
                        15                   20
    Gln-Ser-Phe-Leu-Lys-(Lys)-Leu-(Glu)-Glu-
                        25                   30
    Val-Arg-Lys-Ile-(Gln)-Gly-Val-Gly-Ala-Ala-
    Leu-X  -X-
```

In Run #4, beyond 31 cycles (corresponding to residue 31 in Table III) no further significant sequence information was obtained. In order to obtain a longer unambiguous sequence, in a Run #5, 14 μg of hpG-CSF purified from conditioned medium were reduced with 10 μl of β-mercaptoethanol for one hour at 45° C., then thoroughly dried under a vacuum. The protein residue was then redissolved in 5% formic acid before being applied to a polybrenized glass fiber disc. Sequence analysis was carried out as for Run #4 above. The results of Run #5 are given in Table IV.

TABLE IV

```
    1                   5                    10
    Thr-Pro-Leu-Gly-Pro-Ala-Ser-Ser-Leu-Pro-
                        15                   20
    Gln-Ser-Phe-Leu-Leu-Lys-Cys-Leu-Glu-Gln-
                        25                   30
    Val-Arg-Lys-Ile-Gln-Gly-Asp-Gly-Ala-Ala-
                        35                   40
    Leu-Gln-Phe-Lys-Leu-Gly-Ala-Thr-Tyr-Lys-
                        45
    Val-Phe-Ser-Thr-(Arg)-(Phe)-(Met)-X-
```

The amino acid sequence give in Table IV was sufficiently long (44 residues) and unambiguous to construct probes for obtaining hpG-CSF cDNA as described infra.

EXAMPLE 2

Among standard procedures for isolating cDNA sequences of interest is the preparation of plasmid-borne cDNA "libraries" derived from reverse transcription of mRNA abundant in donor cells selected on the basis of their expression of a target gene. Where substantial portions of the amino acid sequence of a polypeptide are known, labelled, single-stranded DNA probe sequences duplicating a sequence putatively present in the "target" cDNA may be employed in DNA/DNA hybridization procedures carried out on cloned copies of the cDNA which have been denatured to single stranded form. Weissman, et al., U.S. Pat. No. 4,394,443; Wallace, et al., *Nucleic Acids Res.*, 6, 3543–3557 (1979), and Reyes, et al., *Proc. Natl. Acad. Sci. (USA)*, 79, 3270–3274 (1982), and Jaye, et al., *Nucleic Acids Res.*, 11, 2325–2335 (1983). See also, U.S. Pat. No. 4,358,535 to Falkow, et al., relating to DNA/DNA hybridization procedures in effecting diagnosis; and Davis, et al., "A Manual for Genetic Engineering, Advanced Bacterial Genetics", Cold Spring Harbor Laboratory, Cold Spring Harbor, N.Y. (1980) at pp. 55–58 and 174–176, relating to colony and plaque hybridization techniques.

Total RNA was extracted from approximately 1 gram of cells from a bladder carcinoma cell line 5637 (1A6) using a guanidinium thiocyanate procedure for quantitative isolation of intact RNA. [Chirgwin, et al., *Biochemistry*, 18, 5294–5299 (1979)].

The sterile aqueous RNA solution contained total RNA from the IA6 cells. To obtain only the messenger RNA from the total RNA solution, the solution was passed through a column containing oligodeoxy-thymidylate [oligo(dT)] (Collaborative Research, Inc., Waltham, Mass. Poly-Adenylated (poly-A$^+$) tails characteristic of messenger RNA adhere to the column while ribosomal RNA is eluted. As a result of this procedure, approximately 90 μg of poly-adenylated messenger RNA (poly-A$^+$ mRNA) were isolated. The isolated poly-A$^+$ messenger RNA was pre-treated with methyl-mercury hydroxide (Alpha Ventron, Danvers, Mass.) at a final concentration of 4 mM for 5 minutes at room temperature prior to use in a cDNA reaction. The methylmercury hydroxide treatment denatured interactions of messenger RNA, both with itself and with contaminating molecules that inhibit translation. Payvar, et al., *J.Biol.Chem.*, 258, 7636–7642 (1979).

According to the Okayama procedure [Okayama, et al., *Molecular & Cellular Biology*, 2, 161–170 (1982)], a cDNA bank was prepared using mRNA obtained from IA6 cells. The cDNAs were then transformed by incubation into a host microorganism *E. coli* K-12 strain HB101 for amplification.

EXAMPLE 3

Hybridization probes designed on the basis of the hpG-CSF amino terminal sequence of Table IV consisted of a set of 24 oligonucleotides each being 23 bases in length and containing three inosine residues. The probe oligonucleotides were manufactured according to the procedure of Caruthers, et al., *Genetic Engineering*, 4, 1–17 (1982) and labeled with $\gamma$-$^{32}$P ATP by kinasing with polynucleotide kinase. The probe oligonucleotides, corresponding to the messenger RNA for residues 23–30 of the sequence of Table IV, are illustrated in Table V.

TABLE V hpG-CSF Probes $$5'\ GC\ IGC\ ICC\ {}^{A}_{G}TC\ ICC\ {}^{T}_{C}TG\ {}^{G}_{A}AT\ {}^{T}_{C}TT\ 3'$$
$$T$$

The assignment of neutrality to I's was based on the published work of Takahashi, et al., *Proc. Natl. Acad. Sci.* (USA), 82, 1931–1935 (1985) and Ohtsuka, et al., *J. Biol. Chem.*, 260, 2605–2608 (1985). However, inosine may have a destabilizing effect if base paired with a G or T. In Takahashi, et al., inosines may appear to have a neutral effect because they average out as a group to near neutrality (e.g., three having paired favorably with C and two not favorable to pairing with T).

To test the effect of having I's base pair with G's, control experiments were designed using an N-myc gene sequence and clone. The sequences picked from the N-myc gene had the same overall G and C content at the first two positions of each codon as was prescribed by the hpG-CSF probes. Thus, the N-myc test probes were of the same length, contained I's in the same relative positions and had potentially the same average Tm (62–66° C., not accounting for the 3 or 4 inosine residues included) as the hpG-CSF probes.

Two sets of N-myc test probes were constructed according to the procedure of Caruthers, et al., supra. Set I, as illustrated in Table VI included: 1, a 23 mer with perfect match; 2, in which three third position C's were replaced with I's generating the worst possible case for adding I's; and 3, in which four third position C's were replaced with I's. The second set of test probes was designed to represent a more random distribution of inosine base pairs, that might give an overall neutral base pairing effect. Set II, as illustrated in Table VI, included: 4, containing two I's that will base pair with C's and one with a G; and 5, identical to 4 with the addition of one more I:G base pair.

TABLE VI

N-myc Test Probes

| | |
|---|---|
| 1. | 5'CAC AAC TAT GCC GCC CCC TCC CC3' |
| 2. | 5'CAC AAC TAT GCI GCC CCI TCI CC3' |
| 3. | 5'CAI AAC TAT GCI GCC CCI TCI CC3' |

TABLE VI-continued

N-myc Test Probes

| | |
|---|---|
| 4. | 5'AAC GAG CTG TGI GGC AGI CCI GC3' |
| 5. | 5'AAI GAG CTG TGI GGC AGI CCI GC3' |

Five replica filters containing N-myc DNA sequences and chicken growth hormone DNA sequences (as a negative control) were baked in a vacuum oven for 2 hours at 80° C. prior to hybridization. All filters were hybridized as described in Example 4 for the hpG-CSF probes except the period of hybridization was only 6 hours. Filters were washed three times at room temperature then once at 45° C., 10 minutes each. The filters were monitored with a Geiger counter.

The filter representing N-myc probe 3 gave a very weak signal relative to the other four probed filters and was not washed any further. After a 10 minute 50° C. wash, the Geiger counter gave the following percent signal with probe one being normalized to 100%: Probe 2, 20%; Probe 3 (45° C.], 2%; Probe 4, 92%; and Probe 5, 75%. After a 55° C. wash, the percentages were: Probe 2, 16%; Probe 4, 100%; and Probe 5, 80%. A final wash at 60° C. yielded the following percentages: Probe 2, 1.6%; Probe 4, 90%; and Probe 5, 70%.

Thus, in the presence of three I's, as in probes 2 and 4, up to a 60-fold difference in signal is observed as the theoretical Tm (I's not included in the calculation) is approached [based upon a worst case I base pairing (Probe 2) and a relatively neutral I base pairing case (Probe 4)].

The standardization information gained by the N-myc test hybridizations was utilized in washing and monitoring of the hpG-CSF hybridization as indicated below, to gauge the degree of confidence with which the results of less than stringent washing might be accepted.

EXAMPLE 4

According to the procedure of Hanahan, et al., *J. Mol. Biol.*, 166, 557–580 (1983), bacteria containing recombinants with cDNA inserts as prepared in Example 2 were spread on 24 nitrocellulose filters (Millipore, Bedford, Mass.) laid on agar plates. The plates were then incubated to establish approximately 150,000 colonies which were replica plated to 24 other nitro-cellulose filters. The replicas were incubated until distinct colonies appeared. The bacteria on the filters were lysed on sheets of Whatman 3 MM paper barely saturated with sodium hydroxide (0.5M) for 10 minutes, then blotted with Tris (1M) for 2 minutes, followed by blotting with Tris (0.5M) containing NaCl (1.5M) for 10 minutes. When the filters were nearly dry, they were baked for 2 hours at 80° C. in a vacuum oven prior to nucleic acid hybridization. [Wahl, et al., *Proc. Natl. Acad. Sci.* (USA), 76, 3683–3687 (1979)]; and Maniatis, et al., *Cell*, 81, 163–182 (1976).

The filters were prehybridized for 2 hours at 65° C. in 750 ml of 10× Denhardt's, 0.2% SDS and 6×SSC. The filters were rinsed in 6×SSC, then placed four in a bag and hybridized for 14 hours in 6×SSC and 10× Denhardt's. There was approximately 15 ml of solution per bag containing 50×10$^6$ cpm of $^{32}$p-labeled probe (oligonucleotides).

After hybridization, the filters were washed three times in 6×SSC (1 liter/wash) at room temperature for 10 minutes each. The filters were then washed two times at 45° C. for 15 minutes each, once at 500 for 15 minutes and once at 55°

C. for 15 minutes using 1 liter volumes of 6×SSC. The filters were autoradiographed for 2 hours at −70° C. using an intensifying screen and Kodak XAR-2 film. On this autoradiograph, there were 40–50 positive signals detected including 5 very intense signals.

The areas containing the strongest five signals and an additional five positives were scraped from the master plates and replated for a secondary screening using the same probe mixture under the same conditions. The wash procedure differed in that the high temperature washes consisted of two at 55° C. for 15 minutes each and then one at 60° C. for 15 minutes. Based on the N-myc probe study of Example 3, the final wash temperature in the second screening was raised because the aggregate melting temperature for the 24 23-mers was 60–68° C., similar to that of the N-myc probes. Just after the second 55° C. wash, the filters were left damp and an autoradiograph was made. Comparison of this autoradiograph with a second autoradiograph taken for a similar period of time after a final wash at 60° C. showed that only two of the 10 clones being tested did not suffer a substantial loss in signal in rising from 55–60° C. These two clones were later shown to be of nearly identical lengths and restriction endoclease patterns. One clone designated Ppo2, was selected for sequencing.

Sequencing of the recombinant hpG-CSF cDNA clone, Ppo2, obtained by the above procedure was accomplished by the dideoxy method of Sanger, et al., *Proc. Natl. Acad. Sci. (USA)* 74, 5463–5467 (1977). The single-stranded DNA phage M-13 was used as a cloning vector for supplying single-stranded DNA templates from the double-stranded cDNA clones. The Sanger, et al., method revealed the sequence as set forth in FIG. 2 accompanied by its amino acid translation and a complementary strand in the polypeptide coding region.

The following characteristics of the sequence of FIG. 2 are of note. At the 5' end of the sequence there are shown bases corresponding to those of the poly G cDNA linker. There then occur about five bases (designated as "N") whose sequence could not readily be determined unambiguously by the Sanger, et al. method due to the preceding multiple G's. The sequence thereafter reveals a series of 12 codons encoding a portion of a putative leader sequence for the polypeptide. Based on correspondence to the amino terminal sequence of natural isolates of hpCSF described in Example 1, the initial threonine residue of the putative "mature" form of hpG-CSF is indicated by +1. Mature hpG-CSF is thereafter revealed to include 174 residues as indicated. Following the "stop" codon (the OP codon, TGA) are approximately 856 bases of an untranslated 3' sequence and multiple A's of the poly A "tail". Unique HgiAi, and Apa restriction endonuclease recognition sites, as well as two StuI sites (discussed infra with respect to construction of procaryotic and eucaryotic expression systems) are also designated in FIG. 2. Owing to the lack of asparagine residues in the polypeptide, there are no apparent sites for N-glycosylation. The underscored 6 bases near the end of the 3' untranslated sequence represent a potential polyadenylation site.

It is noteworthy that each of two additional cDNA clones identified by the hybridization procedures described above from among a total of 450,000 clones failed to include DNA encoding the entire leader sequence from the transcription initiation site onward. Indeed, all three hpG-CSF clones terminated in the 5' region at exactly the same site, indicating that secondary structure of the mRNA transcribed severely hinders cDNA formation beyond this site. As a practical matter, therefore, cDNA expression screening such as described in Okayama, et al., *Mol. and Cell. Biol.*, 3, 280–289 (1983) and as actually employed to isolate GM-CSF in Wong, et al., *Science*, 228, 810–814 (1985) could not have readily applied to isolation of hpCSF DNA because such isolation systems ordinarily rely upon the presence of a full length cDNA transcript in the clones assayed.

The above sequence is not readily susceptible for securing direct expression of hpG-CSF in a microbial host. To secure such expression, the hpG-CSF coding region should be provided with an initial ATG codon and the sequence should be inserted in a transformation vector at a site under control of a suitable promoter/-regulator DNA sequence.

EXAMPLE 5

In this example, cDNA encoding hpG-CSF as isolated in the previous example was used to screen a genomic clone. A phage lambda human fetal liver genomic library [prepared according to the procedure of Lawn, et al. *Cell*, 15, 1157–1174 (1978) and obtained from T. Maniatis] was screened using a nick translated probe consisting of two hpG-CSF cDNA fragments isolated by digestion with HgiAI and StuI (HgiAI to StuI, 649 b.p.; StuI to StuI, 639 b.p.). A total of approximately 500,000 phage were plated on 12 (15 cm) petri dishes and plaque lifted and hybridized to probe using the Benton/Davison procedure [Benton, et al., *Science*, 196, 180 (1977)]. A total of 12 positive clones were observed. Three clones (1–3) yielding the strongest signals upon autoradiography in a secondary screening were grown in 1 liter cultures and mapped by restriction enzyme digestion and Southern blotting using a radiolabeled 24-mer oligonucleotide (kinased with $\gamma$-$^{32}$P ATP) 5'CTGCACT-GTCCAGAGTGCACTGTG3'. The mapping results showed that isolates 1 and 3 were identical and 2 contained 2000 additional bases 5' to the hpG-CSF gene. Therefore, clone 2 was used for further characterization. DNA from clone 2 was digested with R1 to release an 8500 bp hpG-CSF containing fragment which was subsequently subcloned into pBR322 and further mapped by restriction endonuclease digests, Southern Blotting, M13 subcloning and sequencing. The sequence obtained is as set out in FIG. 3.

A restriction endonuclease map (approximately 3.4 Kb) of genomic DNA containing the hpG-CSF gene is detailed in FIG. 1. The restriction endonucleases shown in FIG. 1 are: NcoI, N; PstI, P; BamHI, B; ApaI, A; XhoI, X; and Kpn, K. The arrows below the map depict the sequencing strategy used to obtain the genomic sequence. The boxed regions are those found in the cDNA clone with the dashed open ended box representing sequence not present in the cDNA clone, but identified by probing mRNA blots. The identification of coding sequences proposed for exon 1 was carried out by Northern blot analysis. A 24 mer oligonucleotide probe, 5'CAGCAGCTGCAGGGCCATCAGCTT3', spanning the predicted splice junctures for exons 1 and 2 was hybridized to hpG-CSF mRNA in a Northern blot format. The resulting blot shows an mRNA the same size (~1650 bp) as that seen with an exon 2 oligonucleotide probe. This data combined with the ability to direct expression of hpG-CSF from the pSVGM-Ppol vector (Example 9) using the Met initiation codon depicted in FIG. 3, defines the coding sequences contained in exon 1. Exons 2–5 are defined by the coding sequences obtained in the cDNA clone (Ppo2) of the hpG-CSF gene (FIG. 2).

EXAMPLE 6

This example relates to preparation of a manufactured gene encoding hpG-CSF and including *E. coli* preference codons.

Briefly stated, the protocol employed was generally as set out in the disclosure of co-owned Alton, et al., PCT Publication No. WO83/04053, which is incorporated by reference herein. The genes were designed for initial assembly of component oligonucleotides into multiple duplexes which, in turn, were assembled into three discrete sections. These sections were designed for ready amplification and, upon removal from the amplification system, could be assembled sequentially or through a multiple fragment ligation in a suitable expression vector.

The construction of Sections I, II and III is illustrated in Table VII through XIV and FIGS 4–6. In the construction of Section I, as illustrated in Table VII and FIG. 4, oligonucleotides 1–14 were assembled into 7 duplexes (1 and 8); 2 and 9; 3 and 10; 4 and 11; 5 and 12; 6 and 13; and 7 and 14). The 7 duplexes were then ligated to form Section I as shown in FIG. 4. It may also be noted in FIG. 4 that Section I includes an upstream XbaI sticky end and a downstream BamHI sticky end useful for ligation to amplification and expression vectors and for ligation to Section II.

TABLE VII

EChpG-CSFDNA SECTION I

| | |
|---|---|
| CTAGAAAAAACCAAGGAGGTAATAAA | 1 |
| TAATGACTCCATTAGGTCCTGCTTCTTCT | 2 |
| CTGCCGCAAAGCTTTCTGCTGAAATGTCTGG | 3 |
| AACAGGTTCGTAAAATCCAGGGTGACGGT | 4 |
| GCTGCACTGCAAGAAAAACTGTGCGCTA | 5 |
| CTTACAAACTGTGCCATCCGGAAGAGC | 6 |
| TGGTACTGCTGGGTCATTCTCTTGG | 7 |
| CATTATTTATTACCTCCTTGGTTTTTT | 8 |
| GCAGAGAAGAAGCAGGACCTAATGGAGT | 9 |
| TGTTCCAGACATTTCAGCAGAAAGCTTTGCG | 10 |
| CAGCACCGTCACCCTGGATTTTACGAACC | 11 |
| TAAGTAGCGCACAGTTTTTCTTGCAGTG | 12 |
| ACCAGCTCTTCCGGATGGCACAGTTTG | 13 |
| GATCCCAAGAGAATGACCCAGCAGT | 14 |

As illustrated in Tables VII and FIG. 5, in the construction of Section II, oligonucleotides 15–30 were assembled into 8 duplexes (15 and 23; 16 and 24; 17 and 25; 18 and 26; 19 and 27; 20 and 28; 21 and 29; and 22 and 30). These 8 duplexes were then ligated to form Section II, as shown in FIG. 5. As further shown in FIG. 5, Section II has an upstream BamHI sticky end and a downstream EcoRI sticky end useful for ligation to an amplification vector and for ligation to Section I. Near its downstream end, Section II also includes a downstream SstI site useful in the eventual ligation Sections II and III.

TABLE VIII

EChpG-CSFDNA SECTION II

| | |
|---|---|
| GATCCCGTGGGCTCCGCTGTCTTCT | 15 |
| TGTCCATCTCAAGCTCTTCAGCTGGC | 16 |
| TGGTTGTCTGTCTCAACTGCATTCTGGT | 17 |
| CTGTTCCTGTATCAGGGTCTTCTG | 18 |
| CAAGCTCTGGAAGGTATCTCTCCGGA | 19 |
| ACTGGGTCCGACTCTGGACACTCTGCA | 20 |
| GCTAGATGTAGCTGACTTTGCTACTACT | 21 |
| ATTTGGCAACAGATGGAAGAGCTCAAAG | 22 |
| GACAAGAAGACAGCGGAGCCCACGG | 23 |
| ACCAGCCAGCTGAAGAGCTTGAGATG | 24 |
| ACAGACCAGAATGCAGTTGAGACAGACA | 25 |
| CTTGCAGAAGACCCTGATACAGGA | 26 |
| CAGTTCCGGAGAGATACCTTCCAGAG | 27 |
| TAGCTGCAGAGTGTCCAGAGTCGGACC | 28 |

TABLE VIII-continued

EChpG-CSFDNA SECTION II

| | |
|---|---|
| AAATAGTAGTAGCAAAGTCAGCTACATC | 29 |
| AATTCTTTGAGCTCTTCCATCTGTTGCC | 30 |

Finally, Section III was constructed as shown in Tables IX and FIG. 6. For this construction, oligonucleotides 31–42 were assembled into 6 duplexes (31 and 37; 32 and 38; 33 and 39; 34 and 40; 35 and 41; and 36 and 42). The 6 duplexes were then ligated to form Section III as depicted in FIG. 6. As also shown in FIG. 6, Section III includes an upstream BamHI sticky end and a downstream EcoRI sticky end useful for ligating into an amplification vector, and at least in the case of the EcoRI end, into an expression vector. In addition, Section II has an upstream SstI site useful in the eventual ligation of Sections II and III.

TABLE IX

EChpG-CSFDNA SECTION III

| | |
|---|---|
| GATCCAAAGAGCTCGGTATGGCACCAG | 31 |
| CTCTGCAACCGACTCAAGGTGCTATGCCG | 32 |
| GCATTCGCTTCTGCATTCCAGCGTCGTGC | 33 |
| AGGAGGTGTACTGGTTGCTTCTCATCTG | 34 |
| CAATCTTTCCTGGAAGTATCTTACCGTGT | 35 |
| TCTGCGTCATCTGGCTCAGCCGTAATAG | 36 |
| AGAGCTGGTGCCATACCGAGCTCTTTG | 37 |
| ATGCCGGCATAGCACCTTGAGTCGGTTGC | 38 |
| TCCTGCACGACGCTGGAATGCAGAAGCGA | 39 |
| ATTGCAGATGAGAAGCAACCAGTACACC | 40 |
| CAGAACACGGTAAGATACTTCCAGGAAAG | 41 |
| AATTCTATTACGGCTGAGCCAGATGACG | 42 |

The XbaI to BamHI fragment formed by Section I is ligated into an M13mpll phage vector opened with XbaI and BamHI. The vector is then reopened by digestion with BamHI and EcoRI, followed by ligation with the BamHI to EcoRI fragment formed by Section II. At this stage, Sections I and II have been joined in proper orientation. Next, another M13mpll vector is opened by BamHI to EcoRI digestion and then ligated with the BamHI to EcoRI fragment formed by Section III.

The vector containing Sections I and II is digested with XbaI and SstI. Likewise, the vector containing Section III is digested with SstI and EcoRI. Both of the smaller of the two fragments resulting from each digestion are ligated into a plasmid pCFM1156 which is previously opened with XbaI and EcoRI. The product of this reaction is an expression plasmid containing a continuous DNA sequence, as shown in FIG. 7, encoding the entire hpG-CSF polypeptide with an amino terminal methionine codon (ATG) for $E.\ coli$ translation initiation.

Although any suitable vector may be employed to express this DNA, the expression plasmid pCFM1156 may readily be constructed from a plasmid pCFM836, the construction of which is described in published European Patent Application No. 136,490. pCFM836 is first cut with NdeI and then blunt-ended with PolI such that both existing NdeI sites are destroyed. Next, the vector is digested with ClaI and SacII to remove an existing polylinker before ligation to a substitute polylinker as illustrated in FIG. 8. This substitute polylinker may be constructed according to the procedure of Alton, et al., supra. Control of expression in the expression pCFM1156 plasmid is by means of a lambda $P_L$ promoter, which itself may be under the control of a $C_{1857}$ repressor gene (such as is provided in $E.\ coli$ strain K12ΔHtrp).

EXAMPLE 7

This example relates to $E.\ coli$ expression of an hpG-CSF polypeptide by means of a DNA sequence encoding [Met$^{-1}$]

hpCSF. The sequence employed was partially synthetic and partially cDNA-derived. The synthetic sequence employed E. coli preference codons.

Plasmid Ppo2, containing the hpG-CSF gene shown in FIG. 2, was digested with HgiAI and StuI providing an approximately 645 base pair fragment including the gene for mature hpCSF (as shown in FIG. 2) with seven of the leader sequence residue codons at the 5' end and about 100 base pairs of the 3' non-coding region. HgiAI digestion leaves a 5', 4-base sticky end identical to that of PstI, and StuI leaves a blunt end. This allows for ready insertion of the fragment into M13 mp8 (Rf) cut with PstI and with the blunt-end-forming restriction enzyme, HincII. Upon amplification in M13, the hpG-CSF DNA was excised by digestion with ApaI and BamHI which cut, respectively, at the ApaI site spanning the codons for residues +3 to +5 of hpCSF and at a BamHI site "downstream" of the HincII site in the M13 mp8 restriction polylinker. In order to allow for E. coli expression of the hpG-CSF polypeptide, a synthetic fragment was prepared as set out in Table X below.

TABLE X

```
5' - C TAG AAA AAA CCA AGG AGG TAA TAA ATA
     3' - TTT TTT GGT TCC TCC ATT ATT TAT
    XbaI

-1  +1
    Met Thr Pro Leu
    ATG ACA CCT CTG GGC C - 5'
    TAC TGT GGA GAC -3'
                    ApaI
```

As may be determined from analysis of Table X, the linker includes an ApaI sticky end, codons specifying the initial three residues of the amino terminal of hpG-CSF ("restoring" the $Thr^1$, $Pro^2$, $Leu^3$-specifying codons deleted upon ApaI digestion of the M13 DNA described above and employing codons preferentially expressed in E. coli), a translation initiating ATG, a sequence of 24 base pairs providing a ribosome binding site, and an XbaI sticky end.

The expression vector employed for E. coli expression was that described as pCFM536 in European Patent Application No. 136,490, by Morris, published Apr. 10, 1985. (See also, A.T.C.C. 39934, E. coli JM103 harboring pCFM536). Briefly, plasmid pCFM536 was digested with XbaI and BamHI. The hpG-CSF fragment (ApaI/BamHI) and linker (XbaI/ApaI) described above were then ligated thereinto to form a plasmid designated p536Ppo2.

Plasmid p53Ppo2 was transformed into a phage resistant variant of the E. coli AM7 strain which has previously been transformed with plasmid pMW1 (A.T.C.C. No. 39933) harboring a $CI^{857}$ gene. Transformation was verified on the basis of the antibiotic (amp) resistance marker gene carried on the pCFM536 progenitor plasmid. Cultures of cells in LB broth (ampicillin 50 $\mu$g 1 ml) were maintained at 28° C. and upon growth of cells in culture to A600=0.5, hpCSF expression was induced by raising the culture temperature to 42° C. for 3 hours. The final O.D. of the culture was A600=1.2.

The level of expression of hpG-CSF by the transformed cells was estimated on a SDS-polyacrylamide gel stained with coomassie blue dye to be 3–5% of total cellular protein.

Cells were harvested by centrifugation at 3500 g for 10 minutes in a JS-4.2 rotor. Cells at 25% (w/v) in water were broken by passing 3 times through a French Pressure Cell at 10,000 p.s.i. The broken cell suspension was centrifuged at 10,000 g for 15 minutes in a JA-20 rotor. The pellet was resuspended in water and solubilized at about 5 mg/ml total protein in 1% lauric acid, 50 mM Tris, pH 8.7. The solubilized pellet material was centrifuged at 15,000 g for 10 minutes and to the supernatant $CuSO_4$ was added to 20 mM. After 1 hour, this sample was loaded onto a C4 HPLC column for purification according to the procedures of example 1 (B) with adjustments made for volume and concentration.

A second purification procedure was developed to yield larger quantities of hpG-CSF formulated in a nonorganic-containing buffer. This material is suitable for in vivo studies. One hundred and fifty grams of cell paste was resuspended in about 600 ml of 1 mM DTT and passed 4 times through a Manton Gualin Homogenizer at about 7000 PSI. The broken cell suspension was centrifuged at 10,000 g for 30 minutes and the pellet was resuspended in 400 ml of 1% deoxycholate (DOC), 5 mM EDTA, 5 mM DTT, and 50 mM Tris, pH 9. This suspension was mixed at room temperature for 30 minutes and centrifuged at 10,000 g for 30 minutes. The pellet was resuspended in about 400 ml of water and centrifuged at 10,000 g for 30 minutes. The pellet was solubilized in 100 ml of 2% Sarkosyl and 50 mM Tris at pH 8. $CuSO_4$ was added to 20 $\mu$M and the mixture was stirred 16 hours at room temperature, and then centrifuged at 20,000 g for 30 minutes. To the supernatant was added 300 ml acetone. This mixture was put on ice for 20 minutes and then centrifuged at 5000 g for 30 minutes. The pellet was dissolved in 250 ml of 6 M guanidine and 40 mM sodium acetate at pH 4, and put over a 1,200 ml G-25 column equilibrated and run in 20 mM sodium acetate at pH 5.4. The hpG-CSF peak (about 400 ml) was pooled and put on a 15 ml CM-cellulose column equilibrated in 20 mM sodium acetate at pH 5.4. After loading, the column was washed with 60 ml of 20 mM sodium acetate at pH 5.4 and with 25 mM sodium chloride, and then the column was eluted with 200 ml of 20 mM sodium acetate at pH 5.4 and with 37 mM sodium chloride. 150 ml of this eluent was concentrated to 10 ml and applied to a 300 ml G-75 column equilibrated and run in 20 mM sodium acetate and 100 mM sodium chloride at pH 5.4. The peak fractions comprising 35 ml were pooled and filter sterilized. The final concentration of hpG-CSF was 1.5 mg/ml, was greater than 95% pure as determined by analysis on a gel, and contained less than 0.5 ng of pyrogen per 0.5 mg of hpG-CSF. The pyrogen level was determined using a Limulus Amebocyte Lysate (LAL) test kit (M. A. Bioproducts, Walkersville, Md.).

EXAMPLE 8

This example relates to the use of recombinant methods to generate analogs of hpG-CSF wherein cysteine residues present at positions 17, 36, 42, 64 and 74 were individually replaced by a suitable amino acid residue.

Site directed mutagenesis procedures according to Souza, et al., published PCT Application No. WO85/00817, published Feb. 28, 1985, were carried out on [$Met^{-1}$] encoding DNA of plasmid p536Ppo2, described infra, using synthetic oligonucleotides ranging in size from 20 to 23 bases as set out in Table XI below. Oligonucleotide No. 1 allowed for formation of a gene encoding [$Ser^{17}$]hpG-CSF; oligonucleotide No. 2 allowed for formation of [$Ser^{36}$]hpG-CSF, and so on.

TABLE XI

| Oligo-nucleotide | Sequence |
|---|---|
| 1. | 5'-CTG CTC AAG TCC TTA GAG CAA GT-3' |
| 2. | 5'-GAG AAG CTG TCT GCC ACC TACA-3' |
| 3. | 5'-TAC AAG CTG TCC CAC CCC GAG-3' |
| 4. | 5'-TGA GCA GCT CCC CCA GCC AG-3' |
| 5. | 5'-CTG GCA GGC TCC TTG AGC CAA-3' |

The Cys to Ser site directed mutagenesis restrictions were carried out using M13 mp10 containing an XbaI-BamHI hpG-CSF fragment isolated from p536Ppo2 as a template. DNA from each M13mp10 clone containing a Cys-Ser substitution was treated with XbaI and BamHI. The resulting fragment was cloned into expression vector pCFM746 and expression products were isolated as in Example 7.

The plasmid pCFM746 may be constructed by cleaving a plasmid pCFM736 (the construction of which from deposited and publically available materials is described in Morris, published PCT Application No. WO85/00829, published Feb. 28, 1985) with ClaI and BamHI to remove an existing polylinker and by substituting the following polylinker.

TABLE XII

```
     ClaI
5' CGATTTGATTCTAGAATTCGTTAACGGTACCATGGAA
3'   TAAACTAAGATCTTAAGCAATTGCCATGGTACCTT
     GCTTACTCGAGGATCCGCGGATAAATAAGTAAC 3'
     CGAATGAGCTCCTAGGCGCCTATTTATTCATTGCTAG 5'
                                          Sau3a
```

In a purification procedure for Cys to Ser analogs according to the present invention, about 10–15 g of cell paste was resuspended in 40 ml of 1 mM DTT and passed 3 times through a French Pressure Cell at 10,000 psi. The broken cell suspension was centrifuged at 1,000 g for 30 minutes. The pellet was resuspended in 1% DOC, 5 mM EDTA, 5 mM DTT, 50 mM Tris, pH 9 and allowed to mix 30 minutes at room temperature. The mixture was centrifuged at 10,000 g for 30 minutes, resuspended in 40 ml $H_2O$, and recentrifuged at 10,000 g for 30 minutes. The pellet was dissolved in 10 ml of 2% Sarkosyl, 50 mM DTT, 50 mM Tris, pH 8. After mixing for 1 hour, the mixture was clarified by centrifugation at 20,000 g for 30 minutes, and then applied to a 300 ml G-75 column equilibrated and run in 1% Sarkosyl, 50 mM Tris, pH 8. Fractions containing the analog were pooled and allowed to air oxidize by standing with exposure to air for at least one day. Final concentrations ranged from 0.5–5 mg/ml.

EXAMPLE 9

In this example, a mammalian cell expression system was devised to ascertain whether an active polypeptide product of hpG-CSF DNA could be expressed in and secreted by mammalian cells (COS-1, A.T.C.C. CRL-1650). This system was designed to provide for secretion of a polypeptide analog of hpG-CSF via expression and secretory processing of a partially synthetic, partially cDNA-derived construction encoding [Ala[1]] hpG-CSF preceded by a leader polypeptide having the sequence of residues attributed to human GM-CSF in Wong, et al., *Science*, 228, 810–815 (1985) and Lee, et al., *Proc. Natl. Acad. Sci. (USA)*, 82, 4360–4364 (1985).

The expression vector employed for preliminary studies of expression of polypeptide products of the invention was a "shuttle" vector incorporating both pBR322 and SV40 DNA which had been designed to allow for autonomous replication in both *E. coli* and mammalian cells, with mammalian cell expression of inserted exogenous DNA under control of a viral promoter/regulator DNA sequence. This vector, designated pSVDM-19, harbored in *E. coli* I 101, was deposited Aug. 23, 1985, with the Americdn Type Culture Collection, 12301 Parklawn Drive, Rockville, Md., and received the accession No. A.T.C.C. 53241.

The specific manipulations involved in the expression vector construction were as follows. A leader-encoding DNA sequence was synthesized as set out in Table XIII below.

TABLE XIII

```
                                          -17
                    HindIII                Met Trp
         5' - A GCT TCC AAC ACC ATG TGG
              3' - AGG TTG TGG TAC ACC
                              -10
         Leu Gln Ser Leu Leu Leu Leu Gly Thr Val
         CTG CAG AGC CTG CTG CTC TTG GGC ACT GTG
         GAC GTC TCG GAC GAC GAG AAC CCG TGA CAC
                         -1  +1
         Ala Cys Ser Ile Ser Ala Pro Leu
         GCC TGC AGC ATC TCT GCA CCC CTG GGC G -3'
         CGG ACG TCG TAG AGA CGT GGG GAC -5'
                                          ApaI
```

As indicated in Table VIII, the sequence includes HindIII and ApaI sticky ends and codons for the 17 amino acid residues attributed to the "leader" of human GM-CSF. There follow codons specifying an alanine residue, a proline residue and a leucine residue. The proline and leucine residues duplicate the amino acids present at positions +2 and +3 of hpG-CSF, while the alanine residue is duplicative of the initial amino terminal (+1) residue of GM-CSF rather than hpG-CSF. Replacement of threonine by alanine was designed to be facilitative of proper host cell "processing off" of the GM-CSF leader by cellular mechanisms ordinarily involved in GM-CSF secretory processing.

Plasmid pSVDM-19 was digested with KpnI and the site was blunt ended with Klenow enzyme. Thereafter the DNA was cut with HindIII. The resulting large fragment was combined and ligated with the HindIII/PvuII fragment shown in FIG. 2 (isolated from plasmid Ppo2 as the second largest fragment resulting from HindIII digestion and partial digestion with PvuII) to form plasmid pSV-Ppol. The manufactured GM-CSF leader sequence fragment of FIG. 3 was then ligated into pSV-Ppol (following its cleavage with HindIII and ApaI) to yield plasmid pSVGM-Ppol.

Calcium phosphate precipitates (1–5µg) of plasmid pSVGM-Ppol DNA was transformed into duplicate 60 mm plates of COS-1 cells essentially as described in Wigler, et al., *Cell*, 14, 725–731 (1978). As a control, plasmid pSVDM-19 was also transformed into COS-1 cells. Tissue culture supernatants were harvested 5 days post-transfection and assayed for hpG-CSF activity. Yields of [Ala[1]]hpG-CSF from the culture supernatant were on the order of 1 to 2.5 µg/ml.

Following successful expression of the [Ala[1]]hpG-CSF product encoded plasmid pSVGM-Ppol in COS-1 cells, another vector was constructed which included the human GM-CSF leader sequence but had a codon for a threonine residue (naturally occurring at position 1 of hpG-CSF) replacing the codon for alanine at that position. Briefly, an oligonucleotide was synthesized (5' CAGCATCTCTACACCTCTGGG) for site-directed mutagenesis (SDM). The HindIII to BamHI hpG-CSF fragment in pSVGM-Ppol was ligated into M13mp10 for the SDM. The newly synthesized hpG-CSF gene containing a Thr codon in position one was isolated by cleavage with HindIII and EcoRI. The fragment was then cloned into pSVDM-19 prepared by cleavage with the same two restriction endonucleases. The resulting vector pSVGM-Ppo(Thr) was transformed into COS cells and the yields of hpG-CSF measured in the culture supernates ranged from 1 to 5 µg/ml.

Finally, the genomic sequence whose isolation is described in Example 5 was employed to form an expression vector for mammalian cell expression of hpG-CSF. More specifically, pSVDM-19 was digested with KpnI and HindIII and the large fragment used in a four-way ligation with a synthetic linker with HindIII and NcoI sticky ends, as shown in Table XIV. An NcoI-BamHI fragment containing exon 1 isolated from pBR322 (8500 hpG-CSF), a genomic subclone, and a BamHI-KpnI fragment containing exons 2–5 isolated from the plasmid pBR322 (8500 hpG-CSF genomic subclone). The resulting mammalian expression vector, pSV/ghG-CSF produced 1 to 2.5 µg/ml of hpG-CSF from transformed COS cells.

TABLE XIV

EXAMPLE 10

This example relates to physical and biological properties or recombinant polypeptide products of the invention.

1. Molecular Weight

Recombinant hpG-CSF products of *E. coli* expression as in Example 7 had an apparent molecular weight of 18.8 kD when determined in reducing SDS-PAGE (as would be predicted from the deduced amino acid analysis of FIG. 2, whereas natural isolates purified as described in Example 1 had an apparent molecular weight of 19.6 kD. The presence of N-glycans associated with the natural isolates could effectively be ruled out on the basis of the lack of asparagine residues in the primary sequence of hpG-CSF in FIG. 2 and therefore a procedure was devised to determine if O-glycans were responsible for molecular weight differences between natural isolates and the non-glycosylated recombinant products. Approximately 5 µg of the natural isolate material was treated with neuraminidase (Calbiochem, LaJolla, Calif.), a 0.5 µg sample was removed, and the remaining material was incubated with 4 mU O-Glycanase (endo-x-n-acetylgalactoseaminidase, Genzyme, Boston, Mass.) at 37° C. Aliquots were removed after ½, 2 and 4 hours of incubation. These samples were subjected to SDS-PAGE side by side with the *E. coli* derived recombinant material. After neuraminidase treatment, the apparent molecular weight of the isolate shifted from 19.6 kD to 19.2 kD, suggestive of removal of a sialic acid residue. After 2 hours of treatment with O-glycanase, the molecular weight shifted to 18.8 kD—identical to the apparent molecular weight of the *E. coli* derived material. The sensitivity of the carbohydrate structure to neuraminidase and O-glycanase suggests the following structure for the carbohydrate component: N-acetylneuraminic acid-a(2–6)galactose, β (1–3) N-acetylgalactoseamine-R, wherein R is serine or threonine.

2. ³H-Thymidine Uptake

Proliferation induction of human bone marrow cells was assayed on the basis of increased incorporation of ³H-thymidine. Human bone marrow from healthy donors was subjected to a density cut with Ficoll-Hypaque (1.077 g/ml, Pharmacia) and low density cells were suspended in Iscove's medium (GIBCO) containing 10% fetal bovine serum and glutamine pen-strep. Subsequently, 2×10⁴ human bone marrow cells were incubated with either control medium or the recombinant *E. coli* material of Example 7 in 96 flat bottom well plates at 37° C. in 5% $CO_2$ in air for 2 days. The samples were assayed in duplicate and the concentration varied over a 10,000 fold range. Cultures were then pulsed for 4 hours with 0.5 µ Ci/well of ³H-Thymidine (New England Nuclear, Boston, Mass.). ³H-Thymidine uptake was measured as described in Ventua, et al., *Blood*, 61, 781 (1983). In this assay human hpG-CSF isolates can induce ³H-Thymidine incorporation into human bone marrow cells at levels approximately 4–10 times higher than control supernatants. The *E. coli*-derived hpG-CSF material of Example 6 had similar properties.

A second human bone marrow cell proliferation study was carried out using culture medium of transfected COS-1 cells as prepared in Example 9 and yielded similar results, indicating that encoded polypeptide products were indeed secreted into culture medium as active materials.

3. WEHI-3B D⁺ Differentiation Induction

Capacity of recombinant, *E. coli*-derived materials to induce differentiation of the murine myelomonocytic leukemic cell line WEHI-3B D⁺ was assayed in semi-solid agar medium as described in Metcalf, *Int. J. Cancer*, 25, 225 (1980). The recombinant hpG-CSF product and media controls were incubated with ~60 WEHI-3B D⁺ cells/well at 37° C. in 5% $CO_2$ in air for 7 days. The samples were incubated in 24 flat bottom well plates and the concentration varied over a 2000-fold range. Colonies were classified as undifferentiated, partially differentiated or wholly differentiated and colony cell counts were counted microscopically. The *E. coli* recombinant material was found to induce differentiation.

4. CFU-GM, BFU-E and CFU-GEMM Assays

Natural isolates of pluripotent human G-CSF (hpG-CSF) and the recombinant pluripotent human G-CSF (rhpG-CSF) were found to cause human bone marrow cells to proliferate and differentiate. These activities were measured in CFU-GM [Broxmeyer, et al., *Exp.Hematol.*, 5, 87, (1971)] BFU-E and CFU-GEMM assays [Lu, et al., *Blood*, 61, 250 (1983)] using low density, non-adherent bone marrow cells from healthy human volunteers. A comparison of CFU-GM, BFU-E and CFU-GEmm biological activities using either 500 units of hpG-CSF or rhpG-CSF are shown in Table XV below.

All the colony assays were performed with low density non-adherent bone marrow cells. Human bone marrow cells were subject to a density cut with Ficoll-Hypaque (density, 1.077 g/cm³; Pharmacia). The low density cells were then resuspended in Iscove's modified Dulbecco's medium containing fetal calf serum and placed for adherence on Falcon tissue culture dishes (No. 3003, Becton Dickenson, Cockeysville, Md.) for 1½ hours at 37° C.

TABLE XV

|  | CFU-GM | BFU-E | CFU-GEMM |
| --- | --- | --- | --- |
| Medium natural | 0 ± 0 | 26 ± 1 | 0 ± 0 |
| hpG-CSF | 83 ± 5.4 | 83 ± 6.7 | 4 ± 0 |
| rhpG-CSF | 87 ± 5 | 81 ± 0.1 | 6 ± 2 |

Medium control consisted of Iscove's modified Dulbecco medium plus 10% FCS, 0.2 mM hemin and 1 unit of recombinant erythropoietin.

For the CFU-GM assay target cells were plated at $1 \times 10^5$ in 1 ml of 0.3% agar culture medium that included supplemented McCoy's 5A medium and 10% heat inactivated fetal calf serum. Cultures were scored for colonies (greater than 40 cells per aggregate) and morphology assessed on day 7 of culture. The number of colonies is shown as the mean ±SEM as determined from quadruplicate plates.

For the BFU-E and CFU-GEMM assays, cells ($1 \times 10^5$) were added to a 1 ml mixture of Iscove's modified Dulbecco medium (Gibco), 0.8% methylcellulose, 30% fetal calf serum 0.05 nM 2-mercaptoethanol, 0.2 mM hemin and 1 unit of recombinant erythriopietin. Dishes were incubated in a humidified atmosphere of 5% $CO_2$ and 5% $O_2$. Low oxygen tension was obtained using an oxyreducer from Reming Bioinstruments (Syracuse, N.Y.). Colonies were scored after 14 days of incubation. The number of colonies is shown as the mean ±SEM, as determined from duplicate plates.

Colonies formed in the CFU-GM assay were all found to be chloracetate esterase positive and non-specific esterase (alpha-naphthyl acetate esterase) negative, consistent with the colonies being granulocyte in type. Both natural hpG-CSF and rhpG-CSF were found to have a specific activity of a approximately $1 \times 10^8$ U/mg pure protein, when assayed by serial dilution in a CFU-GM assay. The BFU-E and CFU-GEMM data in Table XV are representative of three separate experiments and similar to the data reported previously for natural hpG-CSF. It is important to note that the rhpG-CSF is extremely pure and free of other potential mammalian growth factors by virtue of its production in *E. coli*. Thus rhpG-CSF is capable of supporting mixed colony formation (CFU-GEMM) and BFU-E when added in the presence of recombinant erythropoietin.

5. Cell Binding Assays

It was previously reported that WEHI-3B($D^+$) cells and human leukemic cells from newly diagnosed leukemias will bind $^{125}$I-labeled murine G-CSF and that this binding can be competed for by addition of unlabeled G-CSF or human CSF-A. The ability of natural hpG-CSF and rhpG-CSF to compete for binding of $^{125}$I-hpG-CSF to human and murine leukemic cells was tested. Highly purified natural hpG-CSF (>95% pure; 1 µg) was iodinated [Tejedor, et al., *Anal.Biochem.*, 127, 143 (1982)] was separated from reactants by gel filtration and ion exchange chromatography. The specific activity of the natural $^{125}$I-hpG-CSF was approximately 100 protein. Murine WEHI-3B($D^+$) and two human peripheral blood myeloid leukemic cell preparations (ANLL, one classified as M4, the other as M5B) were tested for their ability to bind $^{125}$I-hpG-CSF.

The murine and freshly obtained human peripheral blood myeloid leukemic cells were washed three times with PBS/1% BSA. WEHI-3B($D^+$) cells ($5 \times 10^6$) or fresh leukemic cells ($3 \times 10^6$) were incubated in duplicate in PBS/1% BSA (100 µl) in the absence or presence of various concentrations (volume: 10 µl) of unlabeled hpG-CSF, rhpG-CSF or GM-CSF and in the presence of $^{125}$I-hpG-CSF (approx. 100,000 cpm or 1 ng) at 0° C. for 90 min. (total volume: 120 µl). Cells were then resuspended and layered over 200 µl ice cold FCS in a 350 µl plastic centrifuge tube and centrifuged (1000 g; 1 min.). The pellet was collected by cutting off the end of the tube and pellet and supernatant counted separately in a gamma counter (Packard).

Specific binding (cpm) was determined as total binding in the absence of a competitor (mean of duplicates) minus binding (cpm) in the presence of 100-fold excess of unlabeled hpG-CSF (non-specific binding). The non-specific binding was maximally 2503 cpm for WEHI-3B($D^+$) cells, 1072 cpm for ANLL (M4) cells and 1125 cpm for ANLL (M5B) cells. Experiments one and two were run on separate days using the same preparation of $^{125}$I-hpG-CSF and displayed internal consistency in the percent inhibition noted for 2000 units of hpG-CSF. Data obtained are reported in FIG. 9 below.

As shown in FIG. 9, $^{125}$I-hpG-CSF demonstrated binding to the WEHI-3B($D^+$) leukemic cells. The binding was inhibited in a dose dependent manner by unlabeled natural hpG-CSF or rhpG-CSF, but not by GM-CSF. In addition, binding of natural hpG-CSF to human myelomonocytic leukemic cells (ANLL, M4) was observed. The binding to these cells is paralleled in response to natural hpG-CSF in liquid cultures by differentiation into mature macrophages as judged by morphology. The absence of binding of natural $^{125}$I-hpG-CSF to monocytic leukemic cells from another patient (ANLL, M5B) suggests that certain leukemias may differentially express or lack receptors for hpG-CSF. The ability of rhpG-CSF to compete for the binding of natural $^{125}$I-hpG-CSF, similar to natural hpG-CSF, suggests that the receptors recognize both forms equally well.

These studies demonstrating the binding of natural $^{125}$I-labeled hpG-CSF to leukemic cells are paralleled in culture by the ability of natural hpG-CSF to induce granulocytic and monocytic differentiation of light density bond marrow cells obtained from one patient with an acute promyelocytic leukemia (M3) and a second patient with an acute myeloblastic leukemia (M2). Cells from each patient were cultured for four days in medium alone or in the presence of $1 \times 10^5$ units of rhpG-CSF. Cells from the M3 control cultures incubated in medium alone were still promyelocyte in type; while cells cultured in the presence of rhpG-CSF showed mature cells of the myeloid type including a metamyelocyte, giant band form and segmented meutrophilis and monocyte. The actual differentials for this patient, on 100 cells evaluated for the control, 100% promyelocytes, and for the rhpG-CSF treated cells, 22% blasts plus promyelocytes, 7% myelocytes, 35% metamyelocytes, 20% band forms plus segmented neutrophils, 14% monocytes and 2% macrophages. Of note is the fact that one of the polymorphonuclear granulocytes still contained a prominent auer rod, suggesting that at least this cell represented a differentiated cell belonging to the leukemic clone. Cells from the second patient with a myeloblastic leukemia (M2) were also cultured for four days in the presence or absence of rhpG-CSF. Visual analysis of M2 cells cult ured in medium alone revealed large "blast-like" cells, some of which had nucleoli. Some of the M2 cells, when treated with rhpG-CSF, differentiated to mature segmented neutrophils displaying residual auer rods in the center neutrophil suggesting differentiation occurring in a cell belonging to the leukemic clone. The actual differentiation of 100 cells evaluated morphologically revealed that control cells consisted of 100% blasts. The rhpG-CSF treated cells consisted of 43% blasts, 1% myelocytes, 15% metamyelocytes, 28% band forms plus segmented neutrophils, 2% promonocytes and 11% monocytes. The leukemic cells were also examined for differentiation at four other concentrations of rhpG-CSF ($5\times10^3$, $1\times10^4$, $2.5\times10^4$ and $5\times10^4$ U/ml, data not shown). Even at the lowest c oncentration of rhpG-CSF tested ($5\times10^3$ U/ml), there was significant differentiation (cells differentiated beyond myelocytes) of the M3 (50%) and M2 (37%) leukemic cells .

6. Immunoassay

To prepare polyclonal antibodies for immunoassay use the antigen employed was pluripotent G-CSF purified from the human bladder carcinoma cell line 5637 (1A6) as prepared in Example 1 (B). This material was judged to be 85% pure based on silver nitrate staining of polyacrylamide gels. Six week-old Balb/C mice were immunized with multiple-site subcutaneous injections of antigen. The antigen was resuspended in PBS and emulsified with equal volumes of Freund's complete adjuvant. The dose was 5 to 7 µg of antigen per mouse per injection. A booster immunization was administered 18 days later with the same amount of antigen emulsified with an equal volume of Freund's incomplete adjuvant. 4 days later mouse serum was taken to test for the antibody specific to human pluripotent G-CSF.

Dynatech Immulon II Removawell strips in holders (Dynateck Lab., Inc., Alexandria, Va.) were coated with hpG-CSF 5 µg/ml in 50 mM carbonate-bicarbonate buffer, pH 9.2. Wells were coated with 0.25 µg in a volume of 50 µl . Antigen coated plates were incubated 2 hours at room temperature and overnight at 4° C. The solution was decanted and the plates were incubated 30 minutes with PBS containing 5% BSA to block the reactive surface. This solution was decanted and the diluted preimmune or test sera were added to the wells and incubated for 2 hours at room temperature. Sera were diluted with PBS, pH 7.0 containing 1% BSA. The serum solution was decanted and plates were washed three times with Wash Solution (KPL, Gaithersburg, Md.). Approximately 200,000 cpm of iodinated rabbit anti-mouse IgG (NEN, Boston, Mass.) in 50 µl PBS, pH 7.0 containing 1% BSA was added to each well. After incubating 1½ hours at room temperature, the solution was decanted and plates were washed 5 times with Wash Solution. Wells were removed from holder and counted in a Beckman 5500 gamma counter. High-titered mouse sera showed greater than 12-fold higher reactivity than the corresponding preimmune sera at a dilution of 1:100.

The immunological properties of E. coli-derived hpG-CSF were determined by reactivity to high-titered mouse serum specific to mammalian-cell derived hpG-CSF. 0.25 µg of 90% pure E. coli-derived protein was coated to Immulon II Removawells in a volume of 50 µl and mouse serum was assayed as described above.

High-titered mouse sera showed a 24-fold higher reactivity to the E. coli-derived material than did the corresponding preimmune sera at a dilution of 1:100.

7. Serine Analog Bioassays

[Ser$^{17}$]hpG-CSF, [Ser$^{36}$]hpG-CSF, [Ser$^{42}$]hpG-CSF, [Ser$^{64}$]hpG-CSF, and [Ser$^{74}$]hpG-CSF products prepared according to Example 9 were assayed for hpG-CSF activity in the $^3$H-thymidine uptake, CFU-GM, and WEHI3B D$^+$ assays. In each assay, the (Ser$^{17}$) analog had activity comparable to that of recombinant molecules having the native structure. The remaining analogs had on the order of 100-fold lesser activity in the $^3$H-thymidine uptake assay, 250-fold lesser activity in the CFU-GM assay, and 500-fold lesser activity in the WEHI-3B D$^+$ assay. This data is supportive of the proposition that cysteines at positions 36, 42, 64 and 74 may be needed for full biological activity.

8. In vivo Bioassay

Alzet® osmotic pumps (Alzet Corp., Palo Alto, Calif.; Model 2001) were connected to indwelling right jugular vein catheters and implanted subcutaneously in seven male Syrian golden hamster. Four of the pumps contained a buffer [20 mM sodium acetate (pH 5.4) and 37 mM sodium chloride] and 1.5 mg/ml E. coli-derived hpG-CSF while 3 contained buffer alone. The claimed pumping rate for the osmotic pumps was 1 microliter/hr. for up to seven days. At the third day after implantation of the pumps, the mean granulocyte count of the four treated hamsters was six-fold higher than that of the three (buffer) controls and the increased granulocyte count was reflected in a four-fold increase in total lymphocytes. Erythrocyte count was unchanged by treatment. These results indicate that the recombinant material produces a specific enhancement of production and/or release of granulocytes in a mammal.

In addition to naturally-occurring allelic forms of hpG-CSF, the present invention also embraces other hpG-CSF products such as polypeptide analogs of hpG-CSF and fragments of hpG-CSF. Following the procedures of the above-noted published application by Alton, et al. (WO/83/04053) one may readily design and manufacture genes coding for microbial expression of polypeptides having primary conformations which differ from that herein specified for in terms of the identity or location of one or more residues (e.g., substitutions, terminal and intermediate additions and deletions).

Alternately, modifications of cDNA and genomic genes may be readily accomplished by well-known site-directed mutagenesis techniques and employed to generate analogs and derivatives. Such products would share at least one of the biological properties of hpG-CSF but may differ in others. As examples, projected products of the invention include those which are foreshortened by e.g., deletions; or those which are more stable to hydrolysis (and, therefore, may have more pronounced or longer lasting effects than naturally-occurring); or which have been altered to delete one or more a potential sites for o-glycosylation (which may result in higher activities for yeast-produced products); or which have one or more cysteine residues deleted or replaced by, e.g., alanine or serine residues and are potentially more easily isolated in active form from micrbial systems; or which have one or more tyrosine residues replaced by phenylalanine and may bind more or less readily to hpG-CSF receptors on target cells. Also comprehended are polypeptide fragments duplicating only a part of the continuous amino acid sequence or secondary conformations within hpG-CSF, which fragments may possess one activity of (e.g., receptor binding) and not others (e.g., colony growth stimulating activity).

It is noteworthy that activity is not necessary for any one or more of the products of the invention to have therapeutic utility [see, Weiland, et al., Blut, 44, 173–175 (1982)] or utility in other contexts, such as in assays of hpG-CSF antagonism. Competitive antagonists may be quite useful in, for example, cases of overproduction of hpG-CSF.

According to another aspect of the present invention, the DNA sequence described herein which encodes hpG-CSF polypeptides is valuable for the information which it provides concerning the amino acid sequence of the mammalian protein which has heretofore been unavailable despite analytical processing of isolates of naturally-occurring products. The DNA sequences are also conspicuously valuable as products useful in effecting the large scale microbial synthesis of hpG-CSF by a variety of recombinant techniques. Put another way, DNA sequences provided by the invention are useful in generating new and useful viral and circular plasmid DNA vectors, new and useful transformed and transfected microbial procaryotic and eucaryotic host cells (including bacterial and yeast cells and mammalian cells grown in culture), and new and useful methods for cultured growth of such microbial host cells capable of expression of hpG-CSF and its related products. DNA sequences of the invention are also conspicuously suitable materials for use as labelled probes in isolating hpG-CSF and related protein encoding human genomic DNA as well as cDNA and genomic DNA sequences of other mammalian species. DNA sequences may also be useful in various alternative methods of protein synthesis (e.g., in insect cells) or in genetic therapy in humans and other mammals. DNA sequences of the invention are expected to be useful in developing transgenic mammalian species which may serve as eucaryotic "hosts" for production of hpG-CSF and hpG-CSF products in quantity.

See, generally, Palmiter, et al., *Science*, 222(4625), 809–814 (1983).

Of applicability to hpG-CSF fragments and polypeptide analogs of the invention are reports of the immunological activity of synthetic peptides which substantially duplicate the amino acid sequence extant in naturally-occurring proteins, glycoproteins and nucleoproteins. More specifically, relatively low molecular weight polypeptides have been shown to participate in immune reactions which are similar in duration and extent to the immune reactions of physiologically significant proteins such as viral antigens, polypeptide hormones, and the like. Included among the immune reactions of such polypeptides is the provocation of the formation of specific antibodies in immunologically active animals. See, e.g., Lerner, et al., *Cell*, 23, 309–310 (1981); Ross, et al., *Nature*, 294, 654–656 (1981); Walter, et al., *Proc. Natl. Acad. Sci.* (*USA*), 77, 5197–5200 (1980); Lerner, et al., *Proc. Natl. Acad. Sci.* (*USA*), 78, 3403–3407 (1981); Walter, et al., *Proc. Natl. Acad. Sci.* (*USA*), 78, 4882–4886 (1981); Wong, et al., *Proc. Natl. Acad. Sci.* (*USA*), 78, 7412–7416 (1981); Green, et al., *Cell*, 28, 477–487 (1982); Nigg, et al., *Proc. Natl. Acad. Sci.* (*USA*), 79, 5322–5326 (1982); Baron, et al., *Cell*, 28, 395–404 (1982); Dreesman, et al., *Nature*, 295, 185–160 (1982); and Lerner, *Scientific American*, 248, No. 2, 66–74 (1983). See, also, Kaiser, et al., *Science*, 223, 249–255 (1984) relating to biological and immunological activities of synthetic peptides which approximately share secondary structures of peptide hormones but may not share their primary structural conformation.

While the present invention has been described in terms of preferred embodiments, it is understood that variations and modifications will occur to those skilled in the art. Therefore, it is intended that the appended claims cover all such equivalent variations which come within the scope of the invention as claimed.

What is claimed is:

1. A pharmaceutical composition comprising:
   (a) a therapeutically effective amount of a G-CSF polypeptide product, wherein said G-CSF polypeptide is selected from the group consisting of those containing
       (i) amino acids 1–174, optionally with a methionyl residue at position-1 as shown in FIG. 7;
       (ii) the polypeptide of subpart (i) wherein the cysteinyl residue at position 17 is replaced with an amino acid selected from the group consisting of serine and alanine; and
   (b) optionally an additional composition selected from a hematopoietic factor and a drug.

2. The pharmaceutical composition according to claim 1 wherein said additional hematopoietic factor is IL-3.

3. The pharmaceutical composition according to claims 1 or 2 wherein said additional composition is useful in the treatment of hematopoietic deficits arising from chemotherapy or from radiation therapy.

* * * * *